(12) United States Patent
Houghton et al.

(10) Patent No.: US 8,178,086 B2
(45) Date of Patent: May 15, 2012

(54) ACTIVATION OF HCV SPECIFIC T CELLS

(75) Inventors: Michael Houghton, Danville, CA (US); Yin-Ling Lin, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 511 days.

(21) Appl. No.: 12/087,330

(22) PCT Filed: Jan. 4, 2007

(86) PCT No.: PCT/US2007/000362
§ 371 (c)(1),
(2), (4) Date: Aug. 24, 2009

(87) PCT Pub. No.: WO2007/081848
PCT Pub. Date: Jul. 19, 2007

(65) Prior Publication Data
US 2010/0034844 A1    Feb. 11, 2010

Related U.S. Application Data

(60) Provisional application No. 60/756,354, filed on Jan. 4, 2006, provisional application No. 60/799,840, filed on May 11, 2006, provisional application No. 60/840,082, filed on Aug. 25, 2006.

(51) Int. Cl.
*A61K 39/295* (2006.01)
*A61K 38/00* (2006.01)

(52) U.S. Cl. .................... 424/93.1; 424/196.11
(58) Field of Classification Search .................. None
See application file for complete search history.

(56) References Cited

U.S. PATENT DOCUMENTS

| | | | |
|---|---|---|---|
| 6,482,792 B2 | 11/2002 | Ip | |
| 6,514,731 B1 | 2/2003 | Valenzuela et al. | |
| 7,329,408 B2 * | 2/2008 | Houghton et al. | 424/228.1 |
| 2002/0002272 A1 * | 1/2002 | Houghton et al. | 530/388.3 |
| 2003/0148262 A1 | 8/2003 | Polo et al. | |
| 2003/0232324 A1 | 12/2003 | Polo et al. | |
| 2005/0074465 A1 | 4/2005 | Houghton et al. | |
| 2006/0088819 A1 | 4/2006 | Houghton et al. | |

OTHER PUBLICATIONS

Perri, et al., "An alphavirus replicon particle chimera derived from venezuelan equine encephalitis and sindbis viruses is a potent gene-based vaccine delivery vector," *J Virol* 77:10394-10403 (2003).

* cited by examiner

*Primary Examiner* — Bao Li
(74) *Attorney, Agent, or Firm* — Kenneth M. Goldman; Roberta L. Robins; Robert Gorman

(57) ABSTRACT

Methods for activating HCV-specific T cells are described. The methods utilize one or more administrations of HCV protein compositions, followed by one or more administrations of a viral vector comprising a nucleic acid encoding a least one HCV epitope that is present in the first composition. The protein compositions can further comprise an immunostimulatory nucleic acid and or other adjuvants and immune stimulatory compounds.

18 Claims, 17 Drawing Sheets

MATURE E1
SerPheSerIlePheLeuLeuAlaLeuLeuSerCysLeuThrValProAlaSerAlaTyr 192
TCTTTCTCTATCTTCCTTCTGGCCCTGCTCTCTTGTTGACTGTGCCCGCTTCGGCCTAC
AGAAAGAGATAGAAGGAAGACCGGGACGAGAGAACGAACTGACACGGGCGAAGCCGGATG

GlnValArgAsnSerThrGlyLeuTyrHisValThrAsnAspCysProAsnSerSerIle 212
CAAGTGCGCAACTCCACGGGGCTCTACCACGTCACCAATGATTGCCCTAACTCGAGTATT
GTTCACGCGTTGAGGTGCCCCGAGATGGTGCAGTGGTTACTAACGGGATTGAGCTCATAA

ValTyrGluAlaAlaAspAlaIleLeuHisThrProGlyCysValProCysValArgGlu 232
GTGTACGAGGCGGCCGATGCCATCCTGCACACTCCGGGGTGCGTCCCTTGCGTTCGCGAG
CACATGCTCCGCCGGCTACGGTAGGACGTGTGAGGCCCCACGCAGGGAACGCAAGCGCTC

GlyAsnAlaSerArgCysTrpValAlaMetThrProThrValAlaThrArgAspGlyLys 252
GGCAACGCCTCGAGGTGTTGGGTGGCGATGACCCCTACGGTGGCCACCAGGGATGGCAAA
CCGTTGCGGAGCTCCACAACCCACCGCTACTGGGGATGCCACCGGTGGTCCCTACCGTTT

LeuProAlaThrGlnLeuArgArgHisIleAspLeuLeuValGlySerAlaThrLeuCys 272
CTCCCCGCGACGCAGCTTCGACGTCACATCGATCTGCTTGTCGGGAGCGCCACCCTCTGT
GAGGGGCGCTGCGTCGAAGCTGCAGTGTAGCTAGACGAACAGCCCTCGCGGTGGGAGACA

SerAlaLeuTyrValGlyAspLeuCysGlySerValPheLeuValGlyGlnLeuPheThr 292
TCGGCCCTCTACGTGGGGGACCTGTGCGGGTCTGTCTTTCTTGTCGGCCAACTGTTTACC
AGCCGGGAGATGCACCCCCTGGACACGCCCAGACAGAAAGAACAGCCGGTTGACAAATGG

PheSerProArgArgHisTrpThrThrGlnGlyCysAsnCysSerIleTyrProGlyHis 312
TTCTCTCCCAGGCGCCACTGGACGACGCAAGGTTGCAATTGCTCTATCTATCCCGGCCAT
AAGAGAGGGTCCGCGGTGACCTGCTGCGTTCCAACGTTAACGAGATAGATAGGGCCGGTA

IleThrGlyHisArgMetAlaTrpAspMetMetMetAsnTrpSerProThrThrAlaLeu 332
ATAACGGGTCACCGCATGGCATGGGATATGATGATGAACTGGTCCCCTACGACGGCGTTG
TATTGCCCAGTGGCGTACCGTACCCTATACTACTACTTGACCAGGGGATGCTGCCGCAAC

ValMetAlaGlnLeuLeuArgIleProGlnAlaIleLeuAspMetIleAlaGlyAlaHis 352
GTAATGGCTCAGCTGCTCCGGATCCCACAAGCCATCTTGGACATGATCGCTGGTGCTCAC
CATTACCGAGTCGACGAGGCCTAGGGTGTTCGGTAGAACCTGTACTAGCGACCACGAGTG

TrpGlyValLeuAlaGlyIleAlaTyrPheSerMetValGlyAsnTrpAlaLysValLeu 372
TGGGGAGTCCTGGCGGGCATAGCGTATTTCTCCATGGTGGGGAACTGGGCGAAGGTCCTG
ACCCCTCAGGACCGCCCGTATCGCATAAAGAGGTACCACCCCTTGACCCGCTTCCAGGAC
                                   E2
ValValLeuLeuLeuPheAlaGlyValAspAlaGluThrHisValThrGlyGlySerAla 392
GTAGTGCTGCTGCTATTTGCCGGCGTCGACGCGGAAACCCACGTCACCGGGGGAAGTGCC
CATCACGACGACGATAAACGGCCGCAGCTGCGCCTTTGGGTGCAGTGGCCCCCTTCACGG

GlyHisThrValSerGlyPheValSerLeuLeuAlaProGlyAlaLysGlnAsnValGln 412
GGCCACACTGTGTCTGGATTTGTTAGCCTCCTCGCACCAGGCGCCAAGCAGAACGTCCAG
CCGGTGTGACACAGACCTAAACAATCGGAGGAGCGTGGTCCGCGGTTCGTCTTGCAGGTC

FIGURE 2A

```
LeuIleAsnThrAsnGlySerTrpHisLeuAsnSerThrAlaLeuAsnCysAsnAspSer   432
CTGATCAACACCAACGGCAGTTGGCACCTCAATAGCACGGCCCTGAACTGCAATGATAGC
GACTAGTTGTGGTTGCCGTCAACCGTGGAGTTATCGTGCCGGGACTTGACGTTACTATCG

LeuAsnThrGlyTrpLeuAlaGlyLeuPheTyrHisHisLysPheAsnSerSerGlyCys   452
CTCAACACCGGCTGGTTGGCAGGGCTTTTCTATCACCACAAGTTCAACTCTTCAGGCTGT
GAGTTGTGGCCGACCAACCGTCCCGAAAAGATAGTGGTGTTCAAGTTGAGAAGTCCGACA

ProGluArgLeuAlaSerCysArgProLeuThrAspPheAspGlnGlyTrpGlyProIle   472
CCTGAGAGGCTAGCCAGCTGCCGACCCCTTACCGATTTTGACCAGGGCTGGGGCCCTATC
GGACTCTCCGATCGGTCGACGGCTGGGGAATGGCTAAAACTGGTCCCGACCCCGGGATAG

SerTyrAlaAsnGlySerGlyProAspGlnArgProTyrCysTrpHisTyrProProLys   492
AGTTATGCCAACGGAAGCGGCCCCGACCAGCGCCCTACTGCTGGCACTACCCCCAAAA
TCAATACGGTTGCCTTCGCCGGGGCTGGTCGCGGGATGACGACCGTGATGGGGGTTTT

ProCysGlyIleValProAlaLysSerValCysGlyProValTyrCysPheThrProSer   512
CCTTGCGGTATTGTGCCCGCGAAGAGTGTGTGTGGTCCGGTATATTGCTTCACTCCCAGC
GGAACGCCATAACACGGGCGCTTCTCACACACACCAGGCCATATAACGAAGTGAGGGTCG

ProValValValGlyThrThrAspArgSerGlyAlaProThrTyrSerTrpGlyGluAsn   532
CCCGTGGTGGTGGGAACGACCGACAGGTCGGGCGCGCCCACCTACAGCTGGGGTGAAAAT
GGGCACCACCACCCTTGCTGGCTGTCCAGCCCGCGCGGGTGGATGTCGACCCCACTTTTA

AspThrAspValPheValLeuAsnAsnThrArgProProLeuGlyAsnTrpPheGlyCys   552
GATACGGACGTCTTCGTCCTTAACAATACCAGGCCACCGCTGGGCAATTGGTTCGGTTGT
CTATGCCTGCAGAAGCAGGAATTGTTATGGTCCGGTGGCGACCCGTTAACCAAGCCAACA

ThrTrpMetAsnSerThrGlyPheThrLysValCysGlyAlaProProCysValIleGly   572
ACCTGGATGAACTCAACTGGATTCACCAAAGTGTGCGGAGCGCCTCCTTGTGTCATCGGA
TGGACCTACTTGAGTTGACCTAAGTGGTTTCACACGCCTCGCGGAGGAACACAGTAGCCT

GlyAlaGlyAsnAsnThrLeuHisCysProThrAspCysPheArgLysHisProAspAla   592
GGGGCGGGCAACAACACCCTGCACTGCCCCACTGATTGCTTCCGCAAGCATCCGGACGCC
CCCCGCCCGTTGTTGTGGGACGTGACGGGGTGACTAACGAAGGCGTTCGTAGGCCTGCGG

ThrTyrSerArgCysGlySerGlyProTrpIleThrProArgCysLeuValAspTyrPro   612
ACATACTCTCGGTGCGGCTCCGGTCCCTGGATCACACCCAGGTGCCTGGTCGACTACCCG
TGTATGAGAGCCACGCCGAGGCCAGGGACCTAGTGTGGGTCCACGGACCAGCTGATGGGC

TyrArgLeuTrpHisTyrProCysThrIleAsnTyrThrIlePheLysIleArgMetTyr   632
TATAGGCTTTGGCATTATCCTTGTACCATCAACTACACTATATTTAAAATCAGGATGTAC
ATATCCGAAACCGTAATAGGAACATGGTAGTTGATGTGATATAAATTTTAGTCCTACATG

ValGlyGlyValGluHisArgLeuGluAlaAlaCysAsnTrpThrArgGlyGluArgCys   652
GTGGGAGGGGTCGAGCACAGGCTGGAAGCTGCCTGCAACTGGACGCGGGGCGAACGTTGC
CACCCTCCCCAGCTCGTGTCCGACCTTCGACGGACGTTGACCTGCGCCCCGCTTGCAACG

AspLeuGluAspArgAspArgSerGluLeuSerProLeuLeuLeuThrThrThrGlnTrp   672
GATCTGGAAGATAGGGACAGGTCCGAGCTCAGCCCGTTACTGCTGACCACTACACAGTGG
CTAGACCTTCTATCCCTGTCCAGGCTCGAGTCGGGCAATGACGACTGGTGATGTGTCACC
```

FIGURE 2B

```
GlnValLeuProCysSerPheThrThrLeuProAlaLeuSerThrGlyLeuIleHisLeu  692
CAGGTCCTCCCGTGTTCCTTCACAACCCTGCCAGCCTTGTCCACCGGCCTCATCCACCTC
GTCCAGGAGGGCACAAGGAAGTGTTGGGACGGTCGGAACAGGTGGCCGGAGTAGGTGGAG

HisGlnAsnIleValAspValGlnTyrLeuTyrGlyValGlySerSerIleAlaSerTrp  712
CACCAGAACATTGTGGACGTGCAGTACTTGTACGGGGTGGGGTCAAGCATCGCGTCCTGG
GTGGTCTTGTAACACCTGCACGTCATGAACATGCCCCACCCCAGTTCGTAGCGCAGGACC

AlaIleLysTrpGluTyrValValLeuLeuPheLeuLeuLeuAlaAspAlaArgValCys  732
GCCATTAAGTGGGAGTACGTCGTCCTCCTGTTCCTTCTGCTTGCAGACGCGCGCGTCTGC
CGGTAATTCACCCTCATGCAGCAGGAGGACAAGGAAGACGAACGTCTGCGCGCGCAGACG.
                                                     P7
SerCysLeuTrpMetMetLeuLeuIleSerGlnAlaGluAlaAlaLeuGluAsnLeuVal  752
TCCTGCTTGTGGATGATGCTACTCATATCCCAAGCGGAAGCGGCTTTGGAGAACCTCGTA
AGGACGAACACCTACTACGATGAGTATAGGGTTCGCCTTCGCCGAAACCTCTTGGAGCAT

IleLeuAsnAlaAlaSerLeuAlaGlyThrHisGlyLeuValSerPheLeuValPhePhe  772
ATACTTAATGCAGCATCCCTGGCCGGGACGCACGGTCTTGTATCCTTCCTCGTGTTCTTC
TATGAATTACGTCGTAGGGACCGGCCCTGCGTGCCAGAACATAGGAAGGAGCACAAGAAG

CysPheAlaTrpTyrLeuLysGlyLysTrpValProGlyAlaValTyrThrPheTyrGly  792
TGCTTTGCATGGTATCTGAAGGGTAAGTGGGTGCCCGGAGCGGTCTACACCTTCTACGGG
ACGAAACGTACCATAGACTTCCCATTCACCCACGGGCCTCGCCAGATGTGGAAGATGCCC

MetTrpProLeuLeuLeuLeuLeuLeuAlaLeuProGlnArgAlaTyrAlaOC          809
ATGTGGCCTCTCCTCCTGCTCCTGTTGGCGTTGCCCCAGCGGGCGTACGCGTAA
TACACCGGAGAGGAGGACGAGGACAACCGCAACGGGGTCGCCCGCATGCGCATT
```

FIGURE 2C

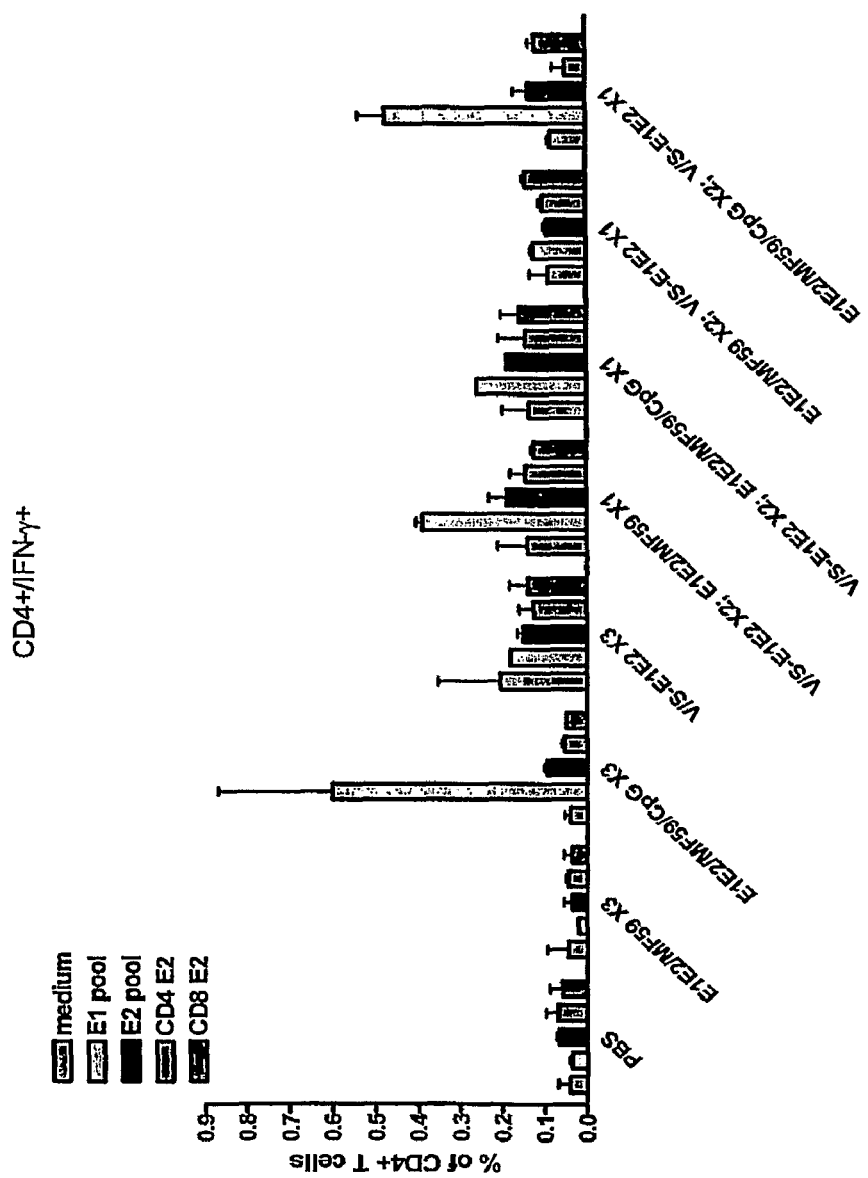

ACTIVATION OF HCV SPECIFIC T CELLS

CROSS REFERENCE TO RELATED APPLICATIONS

This application is a §371 filing from PCT US2007/000362, filed Jan. 4, 2007, and claims the benefit under 35 U.S.C. §119(e)(1) of U.S. Provisional Application Nos. 60/756,354, filed Jan. 4, 2006; 60/799,840, filed May 11, 2006; and 60/840,082, filed Aug. 25, 2006, which applications are incorporated herein by reference in their entireties and from which applications priority is claimed pursuant to the provisions of 35 U.S.C. §§119/120.

TECHNICAL FIELD

The present invention relates to the activation of hepatitis C virus (HCV)-specific T cells. More particularly, the invention relates to immunizing a subject using HCV protein compositions that include HCV E1E2 complexes and or proteins comprising HCV non-structural genes' and subsequently boosting the immune response using a viral vector comprising nucleic acid compositions encoding HCV E1E2 complexes and or HCV non-structural genes, to stimulate humoral and cell-mediated immune responses, such as, e.g., to activate HCV-specific T cells and elicit antibodies that neutralize infectivity of HCV virus.

BACKGROUND

Hepatitis C virus (HCV) was identified over a decade ago and is now known to be the leading cause of non-A and non-B viral hepatitis (Choo et al., *Science* (1989) 244:359-362; Armstrong et al., *Hepatology* (2000) 31:777). HCV infects approximately 3% of the world population, an estimated 200 million people (Cohen, J., *Science* (1999) 285:26). About 30,000 newly acquired HCV infections occur in the United States annually. Additionally, there is a large incidence of HCV infection in developing countries. Although the immune response is capable of clearing HCV infection, the majority of infections become chronic. Most acute infections remain asymptomatic and liver disease usually occurs only after years of chronic infection.

The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391-2399). The virus encodes a single polyprotein having about 3000 amino acid residues (Choo et al., *Science* (1989) 244:359-362; Choo et al., *Proc. Natl. Acad. Sci. USA* (1991) 88:2451-2455; Han et al., *Proc. Natl. Acad. Sci. USA* (1991) 88:1711-1715).

In particular, as shown in FIG. 1, several proteins are encoded by the HCV genome. The order and nomenclature of the cleavage products of the HCV polyprotein is as follows: $NH_2$—C-E1-E2-p7-NS2-NS3-NS4a-NS4b-NS5a-NS5b-COOH. Another protein (F) has also been identified and results from translational frame-shifting within the C gene. Branch et al., *Semin. Liver Dis.* (2005) 25:105-117. Initial cleavage of the polyprotein is catalyzed by host proteases which liberate three structural proteins, the N-terminal nucleocapsid protein (termed ☐core☐) and two envelope glycoproteins, gpE1 (also known as E) and gpE2 (also known as E2/NS1), as well as nonstructural (NS) proteins that encode the viral enzymes and other activities. The NS regions are termed NS2, NS3, NS4 and NS5. NS2 is an integral membrane protein with proteolytic activity and, in combination with NS3, cleaves the NS2-NS3 junction. The NS3 protease, along with its NS4a cofactor, serves to process the remaining polyprotein. In these reactions, NS3 liberates an NS3 cofactor (NS4a), two proteins (NS4b and NS5a), and an RNA-dependent RNA polymerase (NS5b). Completion of polyprotein maturation is initiated by autocatalytic cleavage at the NS3-NS4a junction, catalyzed by the NS3 serine protease.

E1 is detected as a 32-35 kDa glycoprotein species and is converted by endoglycosidase H into an approximately 18 kDa species. By contrast, E2 glycoprotein displays a complex pattern upon immunoprecipitation consistent with the generation of multiple species (Spaete et al., *Virol.* (1992) 188:819-830; Selby et al., *J. Virol.* (1996) 70:5177-5182; Grakoui et al., *J. Virol.* (1993) 67:1385-1395; Tomei et al., *J. Virol.* (1993) 67:4017-4026.). The HCV envelope glycoproteins E1 and E2 form a stable complex that is co-immunoprecipitable (Grakoui et al., *J. Virol.* (1993) 67:1385-1395; Lanford et al., *Virology* (1993) 197:225-235; Ralston et al., *J. Virol.* (1993) 67:6753-6761).

Full-length E1 and E2 are retained within the endoplasmic reticulum of cells and lack complex carbohydrate when expressed stably or in a transient Vaccinia virus system (Spaete et al., *Virology* (1992) 188:819-830; Ralston et al., *J. Virol.* (1993) 67:6753-6761). Since the E1 and E2 proteins are normally membrane-bound in these expression systems, secreted truncated forms have been produced in order to facilitate purification of the proteins. See, e.g., U.S. Pat. No. 6,121,020. Additionally, intracellular production of E1E2 in Hela cells has been described. See, e.g., International Publication No. WO 98/50556.

The HCV E1 and E2 glycoproteins are of considerable interest because they have been shown to be protective against viral challenge in primate studies. (Choo et al., *Proc. Natl. Acad. Sci. USA* (1994) 91:1294-1298; Houghton, M. and Abrignani, S., *Nature* (2005) 436:961-966). Meunier et al., *Proc. Natl. Acad. Sci. USA* (2005) 102:4560-4565 used retroviral pseudoparticles displaying intact E1 and E2 glycoproteins and found that viral-neutralizing antibodies raised during HCV-1 infections are also able to neutralize HCV genotypes 4, 5 and 6, but have only limited neutralization against HCV genotypes 2 and 3.

Currently, the only available therapies for HCV are IFN-α and ribavirin. Unfortunately, these agents are effective in less than half the patients treated (Poynard et al., *Lancet* (1998) 352:1426; McHutchison et al., *Engl. J. Med.* (1998) 339: 1485). Therefore, there is an urgent need for the development of efficacious vaccines to prevent HCV infection, as well as for immunotherapies to be used as an alternative, or in conjunction with existing therapies.

T cell immunity to HCV may determine the outcome of HCV infection and disease (Missale et al., *J. Clin. Invest.* (1996) 98:706; Cooper et al., *Immunity* (1999) 10:439; and Lechner et al., *J. Exp. Med.* (2000) 191:1499). Virus-specific T cell responses have been shown to play an important role in resolving acute HCV infections (Shoukry et al., *Ann. Rev. Microbiol.* (2004) 58:391-424). One study concluded that individuals displaying predominant Th0/Th1 CD4+ T helper responses resolved their HCV infections, while those with Th2-type responses tended to progress to chronicity (Tsai et al., *Hepatology* (1997) 25:449-458). In addition, it has been shown that there is an inverse correlation between the frequency of HCV-specific cytotoxic T lymphocytes (CTLs) and viral load (Nelson, et al., *J. Immunol.* (1997) 158:1473).

Control of HCV in chimpanzees has been shown to be associated with a Th1 T cell response (Major et al., *J. Virol.* (2002) 76:6586-6595). In the chimpanzee model, strong and multi-specific CD8+ T cell responses have been associated with spontaneous control of HCV, and the emergence of escape mutants has been associated with the development of viral persistence (Weiner et al., *Proc. Natl. Acad. Sci. USA* (1995) 92:2755-2759). Therefore, HCV-specific T cell responses appear to play an important role in controlling HCV infection.

Despite extensive advances in the development of pharmaceuticals against certain viruses like HIV, control of acute and chronic HCV infection has had limited success (Hoofnagle and di Bisceglie (1997) N. Engl. J. Med. 336:347-356). As explained above, the generation of a strong cytotoxic T lymphocyte (CTL) response may be important for the control and eradication of HCV infections. Thus, there is a need in the art for effective methods of inducing strong CTL responses against HCV.

SUMMARY OF THE INVENTION

It is an object of the present invention to provide reagents and methods for stimulating or enhancing an immune response to HCV. Said immune response can provide a protective or therapeutic effect against infection with HCV. Said immune response can be a humoral and or cellular response, such as, e.g., eliciting an immunoglobulin (Ig) response wherein the Ig recognize one or more epitopes of HCV polypeptides and or activating T cells which recognize one or more epitopes of HCV polypeptides. This and other objects of the invention are provided by one or more of the embodiments described below.

In one embodiment, the invention provides a method of stimulating or enhancing an immune response to a first HCV antigen wherein a subject is exposed to an HCV protein antigen and then exposed to a viral vector comprising a DNA encoding at least one epitope from said first HCV antigen. The method comprises priming and boosting with the antigen as a protein prime followed by a boost delivered with a viral vector encoding an epitope from the protein antigen.

In another embodiment, the invention provides a method of boosting an immune response to a first protein antigen to which a subject has previously been exposed, the method comprising boosting the immune response to the first antigen by administering a viral vector encoding a DNA which encodes and expresses at least one epitope from the first antigen when the vector is administered to the subject.

Immunization with E1/E2 HCV heterodimers can elicit neutralizing antibodies to HCV and CpG can enhance the CD4+ T cell response to E1/E2. The present invention provides improved combination prime boost methods that provide both a neutralizing antibody response and T cell responses (CD4+ T cell and CTL) to HCV.

Immunization with HCV NS345 proteins can elicit T cell responses to HCV and CpG can enhance the response. The present invention provides improved combination prime boost methods that provide both a neutralizing antibody response and T cell responses (CD4+ T cell and CTL) to HCV.

In particular, the invention provides methods for stimulating immune responses using a combination of HCV proteins and polynucleotides encoding one or more HCV proteins. In one embodiment, the polynucleotides encoding the proteins are delivered as part of a viral vector particle. In one embodiment, the viral vector particle is an alpahvirus and in a preferred embodiment is a chimeric alpahvirus replicon packaged in a defective alpahvirus particle. In one embodiment, the immune response comprises the activation of HCV-specific T cells. The present invention is based in part, on the surprising discovery that priming immune responses using HCV E1E2 protein vaccines, and boosting with HCV E1E2 nucleic acid constructs delivered in a defective alpahvirus particle, stimulates a robust CD8+ T cell response. Thus, the use of such combinations provides an effective approach for stimulating a cellular and or humoral immune response to HCV E1E2 immunogens.

Additionally, priming with an HCV polyprotein or HCV fusion protein and boosting with alphavirus encoding at least a portion of the same polyprotein or fusion protein can also provide an increased immune response to HCV.

In one embodiment, the invention provides a so called "prime-boost" immunization regimen for eliciting or increasing an immune response to HCV in a subject. In one preferred embodiment, the priming immunization step comprises immunizing a subject with one or more proteins followed by a boosting step comprising immunizing the subject with a viral vector encoding one or more of said proteins. In some embodiments, the viral vector is an alphavirus. In some embodiments, the proteins are HCV proteins. In some embodiments, the subject is a vertebrate subject. In some embodiments, the vertebrate subject is a human. In a preferred embodiment, the proteins are HCV proteins and the viral vector is an alphavirus vector and the subject is a vertebrate animal or vertebrate subject. In some embodiments, the vertebrate animal or vertebrate subject is a human.

In certain embodiments, immunogenic compositions described herein are administered to a mammalian subject and in some embodiments the subject is a human. Priming, as used herein, means any method whereby a first immunization with the immunogenic protein compositions described herein permits the generation of an immune response to the target antigen or antigens upon a second or subsequent immunization (boosting) with virus replicon particles described herein comprising at least one of the same antigen or antigens administered in the priming step, wherein the second immune response is greater than that achieved where the first immunization is either not provided or where the first immunization administered does not comprise the same antigen or antigens administered in the second immunization. Priming encompasses regimens which include a single dose or multiple dosages, administered hourly, daily, weekly, monthly or yearly. In a particular embodiment, priming (or priming immunization) comprises at least two administrations (comprising one or more dose or dosage). For example, in a particular embodiment, priming by administration of one or more immunogenic compositions described herein, entails at least two (e.g., 2, 3, 4, 5, 6, 7 or more) administrations (comprising one or more dose or dosage) of the immunogenic composition(s). The time interval between administrations can be hours, days, weeks, months or years. Further, in certain embodiments, the repeated steps can be performed using the same or different immunogenic compositions.

In some embodiments, the immunogenic compositions described herein are administered as a booster to boost the immune response achieved after priming of the subject. In one preferred embodiment, alphavirus replicon particles are administered as a booster some time after priming. Virus replicon particles administered as a booster comprise a nucleic acid encoding at least one same antigen administered by at least one priming step. In a particular embodiment, boosting (or boosting immunization) is about two (2) to twenty-seven (27) weeks after priming (or priming immunization). Boosting-encompasses regimens which include a single dose or multiple dosages, administered hourly, daily, weekly, monthly or yearly. In certain embodiments, boosting (or boosting immunization) comprises at least one administration. In other embodiments, boosting (or boosting immunization) comprises at least two administrations (comprising one or more dose or dosage). For example, in such instance, in a particular embodiment, boosting by administration of one or more virus replicon particle, entails at least two (e.g., 2, 3, 4, 5, 6, 7 or more) administrations (comprising one or more dose or dosage) of the virus replicon particle(s). The time interval between administrations can be hours, days, weeks, months or years. Further, in certain embodiments, the repeated steps can be performed using the same or different virus replicon particles or immunogenic compositions.

The priming or boosting immunizations can a combination of one or more of intramuscular, mucosal or systemic routes of immunization.

In one preferred embodiment, the invention provides a method of immunization which comprises a priming immunization with an HCV protein antigen followed by a boosting immunization with an alphavirus replicon particle comprising a nucleic acid encoding at least one epitope of the HCV antigen of the priming step. The HCV antigen can comprise on or more different HCV antigens.

In one preferred embodiment, the invention provides the use of a composition as described herein for the preparation of a medicament to be used in a method of immunization which medicament comprises at least one of a priming composition comprising an HCV protein antigen or a boosting composition comprising an alphavirus replicon particle comprising a nucleic acid encoding an HCV antigen to which a subject has already been primed.

In one embodiment, the priming step(s) comprises immunizing a subject with HCV E1/E2 heterodimer and an adjuvant which in one embodiment is MF59, followed by a boosting step comprising immunization with an alphavirus replicon particle comprising a nucleic acid encoding the E1/E2 protein.

In another embodiment, the invention provides a method of immunizing a subject which comprises administering an alphavirus encoding an E1/E2 heterodimer complex, wherein said subject has already been exposed to E1/E2 protein following infection with HCV, whereby the cellular immune response to E1/E2 is increased on the subject.

In another embodiment, the invention provides a method of immunizing a vertebrate which comprises administering an alphavirus encoding an E1/E2 heterodimer complex, wherein said subject has already been exposed to E1/E2 protein following infection with HCV, whereby the cellular immune response to E1/E2 is increased on the subject.

In one embodiment, the priming step(s) comprise immunizing a subject with HCV E1/E2 heterodimer, MF59 and a CpG followed by a boosting step comprising immunization with an alphavirus replicon particle comprising a nucleic acid encoding the E1/E2 protein.

In one embodiment, the priming step(s) comprise immunizing a vertebrate subject with HCV E1/E2 heterodimer, MF59 and a CpG followed by a boosting step comprising immunization with an alphavirus replicon particle comprising a nucleic acid encoding the E1E2 protein.

In one embodiment, the priming step(s) comprise immunizing a subject with HCV polyprotein and an adjuvant which in one embodiment is an ISCOM, followed by a boosting step comprising immunization with an alphavirus replicon particle comprising a nucleic acid encoding at least a portion of the polyprotein. The HCV polyprotein can further be administered in a composition comprising an immunostimulatory molecule, which in one embodiment is a CpG immunostimulatory molecule.

In one embodiment, the priming step(s) comprise immunizing a vertebrate subject with HCV polyprotein and an adjuvant which in one embodiment is an ISCOM, followed by a boosting step comprising immunization with an alphavirus replicon particle comprising a nucleic acid encoding at least a portion of the polyprotein. The HCV polyprotein can further be administered in a composition comprising an immunostimulatory molecule, which in one embodiment is a CpG immunostimulatory molecule.

In another embodiment, the invention provides a method of immunizing a subject which comprises administering an alphavirus encoding an HCV polyprotein, wherein said subject has already been exposed to HCV polyprotein following infection with HCV, whereby the cellular immune response to HCV polyprotein is increased on the subject.

In another embodiment, the invention provides a method of immunizing a vertebrate which comprises administering an alphavirus encoding an HCV polyprotein, wherein said subject has already been exposed to HCV polyprotein following infection with HCV, whereby the cellular immune response to HCV polyprotein is increased on the subject.

The immunization steps of the invention which comprise administration of a protein, the kits and the compositions of the invention all can further comprise administration or inclusion of a CpG or other immunostimulatory molecule and or adjuvant.

In one embodiment, the priming step(s) comprise immunizing a subject with HCV E1/E2 heterodimer, MF59 and a CpG followed by a boosting step comprising immunization with an alphavirus replicon particle comprising a nucleic acid encoding the E1/E2 protein.

In one embodiment, the priming step(s) comprise immunizing a vertebrate subject with HCV E1/E2 heterodimer, MF59 and a CpG followed by a boosting step comprising immunization with an alphavirus replicon particle comprising a nucleic acid encoding the E1/E2 protein.

The polypeptides and nucleotides encoding said polypeptides are derived from the same HCV isolate, or from different strains and isolates including isolates having any of the various HCV genotypes, to provide increased protection against a broad range of HCV genotypes.

In one embodiment, the invention provides a method for treating a subject that has already been exposed to HCV infection (i.e., a vertebrate subject that has already been "primed" by exposure to one or more HCV antigens) with an alphavirus boosting regimen to enhance the immune response to HCV in the vertebrate subject. In other embodiments where a vertebrate subject is already infected with or exposed to HCV, the method of treatment can include one or more priming steps together with one or more boosting steps.

In one embodiment, the invention provides a method for treating a vertebrate subject that has already been exposed to HCV infection (i.e., a vertebrate subject that has already been "primed" by exposure to one or more HCV antigens) with an alphavirus boosting regimen to enhance the immune response to HCV in the vertebrate subject. In other embodiments where a vertebrate subject is already infected with or exposed to HCV, the method of treatment can include one or more priming steps together with one or more boosting steps.

In other embodiments, the invention provides the use of a composition comprising an HCV protein or an alphavirus particle encoding an HCV protein in the manufacture of a medicament for generating an immune response to HCV in a subject by: at least one administration of the protein followed by at least one administration of the alphavirus particle.

In other embodiments, the invention provides the use of a composition comprising an HCV protein or an alphavirus particle encoding an HCV protein in the manufacture of a medicament for generating an immune response to HCV in an individual by: at least one administration of the protein followed by at least one administration of the alphavirus particle.

The present invention also provides a kit for inducing or generating an immune response in a subject such as a mammal. The kit comprises (i) a first composition which comprises HCV protein and an adjuvant; and (ii) a second composition which comprises a viral vector encoding at least a portion of the HCV protein of the first composition. In one preferred embodiment, the adjuvant is an oil in water emulsion that can be MF59. In one embodiment, the first composition in said kit comprises MF59 as an adjuvant. In another embodiment, the first composition comprising E1/E2 protein and MF59 further comprises CpG.

In some embodiments, the kit comprises (i) a first composition which comprises E1E2 protein complexes and an adjuvant; and (ii) a second composition which comprises a viral vector encoding E1E2 protein complexes. In one preferred embodiment, the adjuvant is an oil in water emulsion that can be MF59. In one embodiment, the first composition in said kit comprises MF59 as an adjuvant. In another embodiment, the first composition comprising E1/E2 protein and MF59 further comprises CpG. In one preferred embodiment, the viral vector is a defective alphaviral particle.

The kit can comprise single or multiple doses of the first composition, of the second composition or of both first and second compositions. Thus, in a particular embodiment, to facilitate repeat administrations, the kit can comprise a plurality of vials for one or both compositions, each vial comprising the dose to be administered to the subject at each administration. The kit can further comprise instructions for use of the kit. In other embodiments, the kit can also comprise an applicator for administering the first composition and/or an applicator for administering the second composition to the mammal.

The kits of the invention can further comprise instructions for using the compositions of the kit alone or together with other compositions.

In one embodiment, the invention is directed to a method of stimulating an immune response in a subject or a vertebrate subject, said method comprising:
administering at least once a first composition comprising an HCV protein complex to said subject or vertebrate subject; and
subsequently administering at least once a second composition comprising a viral vector comprising a nucleic acid encoding at least a portion of said HCV protein already administered to said subject or vertebrate subject, whereby the nucleic acid encoding an HCV protein is expressed in one or more cells of the subject and the HCV protein is produced. The immune response can be a cellular and or a humoral immune response. The cellular or humoral immune response can be stimulated using any of the various first protein compositions and second viral vector compositions described herein.

The subject or vertebrate subject may have already been exposed or infected with HCV or may be naïve in regards to exposure to the virus.

In one embodiment, the invention is directed to a method of stimulating an immune response in a subject or vertebrate subject, said method comprising:
administering at least once a first composition comprising an HCV E1E2 protein complex to said subject or vertebrate subject; and
subsequently administering at least once a second composition comprising a viral vector comprising a nucleic acid encoding an HCV E1E2 complex to said subject or vertebrate subject, whereby the nucleic acid encoding an HCV E1E2 complex is expressed in one or more cells of the subject and E1E2 protein complex is produced. The immune response can be a cellular and or a humoral immune response. The cellular or humoral immune response can be stimulated using any of the various first protein compositions and second viral vector compositions described herein.

The E1/E2 protein complexes and or the alphavirus encoding said E1/E2 complexes can be partial or complete protein (or protein-coding in the case of the viral vector) sequences as described further herein. Furthermore, it is not necessary that the exact sequence used as the protein immunization composition is included in the nucleic acid encoding the protein sequence. Either the protein amino acid sequence or nucleic acid encoding the protein sequence can be partial or complete in regards to the HCV genome.

The first and second compositions can be administered one or more times in any variety of combinations, such as for example 1, 2, 3, 4, or 5 or more sequential administrations of the first composition comprising a protein followed by 1, 2, 3, 4 or 5 or more sequential administrations of the second composition comprising a viral vector. Furthermore, administration of the second composition can occur before administration of a second or subsequent first composition.

In another embodiment, the invention provides a method of activating T cells of a subject or vertebrate subject, wherein said T cells recognize an epitope of a hepatitis C virus (HCV) polypeptide, said method comprising:
administering at least once a first composition comprising an HCV E1E2 protein complex to said subject or vertebrate subject; and
subsequently administering at least once a second composition comprising a viral vector comprising a nucleic acid encoding an HCV E1E2 complex to said subject or vertebrate subject, whereby the nucleic acid encoding an HCV E1E2 complex is expressed in one or more cells of the subject and E1E2 protein complex is produced;
whereby T cells are activated in said subject and said activated T cells recognize an epitope of E1, E2 or the E1E2 complex. The viral vector can be a mammalian viral vector such as an alpahvirus vector and in one embodiment the alpahvirus vector is a defective alphavirus vector particle that can be a chimeric alpahvirus defective replicon particle.

The subject or vertebrate subject is either already infected with HCV prior to administration of one or more of said first and second compositions or has not been infected prior to administration. Thus, the methods can provide prophylactic and therapeutic effects.

In a preferred embodiment, the methods stimulate in the activation of the T cells comprise $CD8^+$ T cells, wherein activation includes an increase in the number of CD8+ T-cells producing gamma interferon.

In another embodiment, the methods stimulate in the activation of the T cells comprise $CD4^+$ T cells, wherein activation includes an increase in the number of CD4+ T-cells producing gamma interferon.

In another embodiment, the methods stimulate in the activation of B cells, wherein activation includes an increase in the number of antibodies having a protective of therapeutic effect against HCV.

The first protein compositions can further comprise at least one adjuvant and can comprise more than one adjuvant or an adjuvant and another immunostimulatory composition. One preferred adjuvant is a submicron oil-in-water emulsion. In one embodiment, the submicron oil-in-water emulsion to be added to the protein composition comprises 4-5% w/v squalene, 0.25-1.0% w/v polyoxyelthylenesorbitan monooleate, and/or 0.25-1.0% sorbitan trioleate, and optionally, N-acetylmuramyl-L-alanyl-D-isogluatminyl-L-alanine-2-(1'-2'-dipalmitoyl-sn-glycero-3-huydroxyphosphory-loxy)-ethylamine (MTP-PE). In one embodiment, the submicron oil-in-water emulsion is MF59. One preferred immunostimulatory composition is an immunostimulatory nucleic acid which on one preferred composition is a CpG immunostimulatory nucleic acid.

In a preferred embodiment, the first composition comprising an E1E2 protein can be produced by expression of a polynucleotide encoding a sequence of amino acids having at least 80% sequence identity to the sequence of amino acids depicted at positions 192-809 of FIGS. 2A-2C.

In another preferred embodiment, the second composition comprising a viral vector comprising a nucleic acid encoding an HCV E1E2 complex encodes a sequence of amino acids having at least 80% sequence identity to the sequence of amino acids depicted at positions 192-746 of FIGS. 2A-2C.

The adjuvant and the protein antigen(s) may be administered simultaneously, sequentially or separately. The adjuvant may be administered to prime the subject before administration of the antigen(s) or after the administration of the antigen(s) to boost the immune response to that antigen. The adjuvant and protein antigen(s) are preferably administered in admixture.

The protein antigen(s) and the viral vector may be administered simultaneously, sequentially or separately. The protein composition may be administered to prime the subject before administration of the viral vector. The protein antigen(s) and viral vector are preferably administered sequentially with protein antigen administered at least once before the viral vector is administered. The invention also provides the use of at least one antigen in the manufacture of a medicament for raising an immune response in a patient, wherein the medicament is administered with an adjuvant. Similarly, the invention provides the use of an adjuvant in the manufacture of a medicament for raising an immune response in a patient, wherein the medicament is administered with at least one antigen. Use of a viral vector in the manufacture of a medicament is also provided. These and other embodiments of the subject invention will readily occur to those of skill in the art in view of the disclosure herein.

BRIEF DESCRIPTION OF THE FIGURES

FIGS. 2A-2C (SEQ ID NOS:1 and 2, amino acid sequence on top of each row (SEQ ID NO:2) and double-strand nucleic acid triplet codon sequence on bottom of each row, top strand SEQ ID NO:1) show the nucleotide and corresponding amino acid sequence for the HCV-1 E1/E2/p7 region. The numbers shown in the figure are relative to the full-length HCV-1 polyprotein. The E1 region (amino acids 1-210 of SEQ ID NO:2; mature E1 shown at positions 20-211 of SEQ ID NO:2), E2 region (amino acids 212-574 of SEQ ID NO:2) and p7 region (amino acids 575-637 of SEQ ID NO:2) are shown.

FIG. 5a shows HCV-specific CD4+ and IFN-γ expression in mice vaccinated as described in the legend and examples.

DETAILED DESCRIPTION OF THE INVENTION

Figure 1:
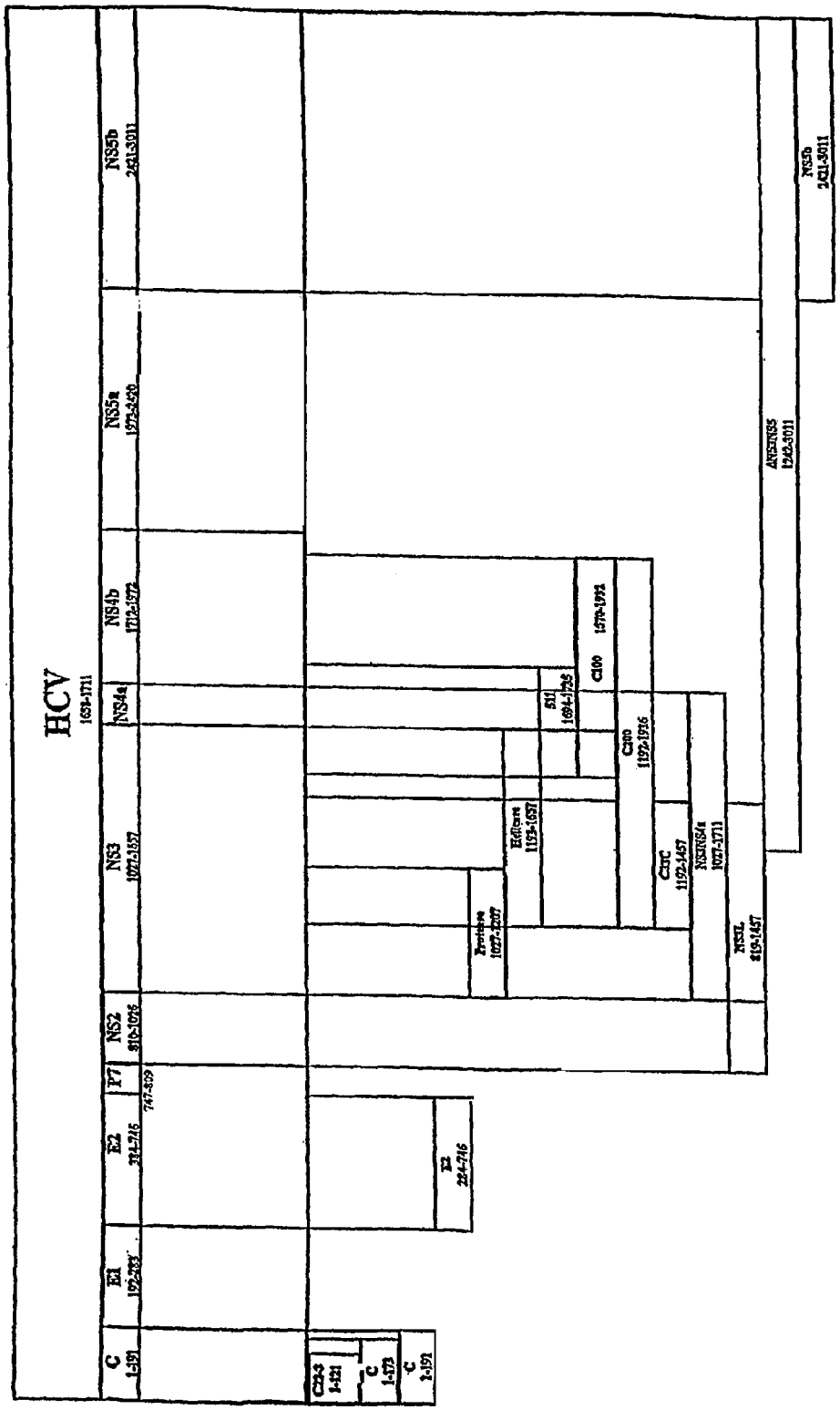
FIG. 1 is a diagrammatic representation of the HCV genome, depicting the various regions of the HCV polyprotein.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

The following amino acid abbreviations are used throughout the text:

Alanine: Ala (A) Arginine: Arg (R)

Asparagine: Asn (N) Aspartic acid: Asp (D)

Cysteine: Cys (C) Glutanine: Gln (Q)

Glutamic acid: Glu (E) Glycine: Gly (G)

Histidine: H is (H) Isoleucine: Ile (I)

Leucine: Leu (L) Lysine: Lys (K)

Methionine: Met (M) Phenylalanine: Phe (F)

Proline: Pro (P) Serine: Ser (S)

Threonine: Thr (T) Tryptophan: Trp (W)

Tyrosine: Tyr (Y) Valine: Val (V)

1. Definitions

In describing the present invention, the following terms will be employed, and are intended to be defined as indicated below.

It must be noted that, as used in this specification and the appended embodiments, the singular forms "a", "an" and "the" include plural referents unless the content clearly dictates otherwise. Thus, for example, reference to "an E1E2 complex" includes a mixture of two or more such complexes, and the like.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By an "E1 polypeptide" is meant a molecule derived from an HCV E1 region. The mature E1 region of HCV-1 begins at approximately amino acid 192 of the polyprotein and continues to approximately amino acid 383, numbered relative to the full-length HCV-1 polyprotein. (See, FIGS. 1 and 2A-2C. Amino acids 192-383 of FIGS. 2A-2C correspond to amino acid positions 20-211 of SEQ ID NO:2.) Amino acids at around 173 through approximately 191 (amino acids 1-19 of SEQ ID NO:2) serve as a signal sequence for E1. Thus, by an "E1 polypeptide" is meant either a precursor E1 protein, including the signal sequence, or a mature E1 polypeptide which lacks this sequence, or even an E1 polypeptide with a heterologous signal sequence. The E1 polypeptide includes a C-terminal membrane anchor sequence-which occurs at approximately amino acid positions 360-383 (see, International Publication No. WO 96/04301, published Feb. 15, 1996). An E1 polypeptide, as defined herein, may or may not include the C-terminal anchor sequence or portions thereof.

By an "E2 polypeptide" is meant a molecule derived from an HCV E2 region. The mature E2 region of HCV-1 begins at approximately amino acid 383-385, numbered relative to the full-length HCV-1 polyprotein. (See, FIGS. 1 and 2A-2C. Amino acids 383-385 of FIGS. 2A-2C correspond to amino acid positions 211-213 of SEQ ID NO:2.) A signal peptide begins at approximately amino acid 364 of the polyprotein. Thus, by an "E2 polypeptide" is meant either a precursor E2 protein, including the signal sequence, or a mature E2 polypeptide which lacks this sequence, or even an E2 polypeptide with a heterologous signal sequence. The E2 polypeptide includes a C-terminal membrane anchor sequence which occurs at approximately amino acid positions 715-730 and may extend as far as approximately amino acid residue 746 (see, Lin et al., *J. Virol.* (1994) 68:5063-5073). An E2 polypeptide, as defined herein, may or may not include the C-terminal anchor sequence or portions thereof. Moreover, an E2 polypeptide may also include all or a portion of the p7 region which occurs immediately adjacent to the C-terminus of E2. As shown in FIGS. 1 and 2A-2C, the p7 region is found at positions 747-809, numbered relative to the full-length HCV-1 polyprotein (amino acid positions 575-637 of SEQ ID NO:2). Additionally, it is known that multiple species of HCV E2 exist (Spaete et al., *Virol.* (1992) 188:819-830; Selby et al., *J. Virol.* (1996) 70:5177-5182; Grakoui et al., *J. Virol.* (1993) 67:1385-1395; Tomei et al., *J. Virol.* (1993) 67:4017-4026). Accordingly, for purposes of the present invention, the term "E2" encompasses any of these species of E2 including, without limitation, species that have deletions of 1-20 or more of the amino acids from the N-terminus of the E2, such as, e.g., deletions of 1, 2, 3, 4, 5 . . . 10 . . . 15, 16, 17, 18, 19 . . . etc. amino acids. Such E2 species include those beginning at amino acid 387, amino acid 402, amino acid 403, etc.

Representative E1 and E2 regions from HCV-1 are shown in FIGS. 2A-2C and SEQ ID NO:2. For purposes of the present invention, the E1 and E2 regions are defined with respect to the amino acid number of the polyprotein encoded by the genome of HCV-1, with the initiator methionine being designated position 1. See, e.g., Choo et al., *Proc. Natl. Acad. Sci. USA* (1991) 88:2451-2455. However, it should be noted that the term an "E1 polypeptide" or an "E2 polypeptide" as used herein is not limited to the HCV-1 sequence. In this regard, the corresponding E1 or E2 regions in other HCV isolates can be readily determined by aligning sequences from the isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc. Natl. Acad. Sci. USA* (1988) 85:2444-2448.

Furthermore, an "E1 polypeptide" or an "E2 polypeptide" as defined herein is not limited to a polypeptide having the exact sequence depicted in the Figures. Indeed, the HCV genome is in a state of constant flux in vivo and contains several variable domains which exhibit relatively high degrees of variability between isolates. A number of conserved and variable regions are known between these strains and, in general, the amino acid sequences of epitopes derived from these regions will have a high degree of sequence homology, e.g., amino acid sequence homology of more than 30%, preferably more than 40%, more than 60%, and even more than 80-90% homology, when the two sequences are aligned. It is readily apparent that the terms encompass E1 and E2 polypeptides from any of the various HCV strains and isolates including isolates having any of the 6 genotypes of HCV described in Simmonds et al., *J. Gen. Virol.* (1993) 74:2391-2399 (e.g., strains 1, 2, 3, 4 etc.), as well as newly identified isolates, and subtypes of these isolates, such as HCV1a, HCV1b etc.

Thus, for example, the term "E1" or "E2" polypeptide refers to native E1 or E2 sequences from any of the various HCV strains, as well as analogs, muteins and immunogenic fragments, as defined further below. The complete genotypes of many of these strains are known. See, e.g., U.S. Pat. No. 6,150,087 and GenBank Accession Nos. AJ238800 and AJ238799.

Additionally, the terms "E1 polypeptide" and "E2 polypeptide" encompass proteins which include modifications to the native sequence, such as internal deletions, additions and substitutions (generally conservative in nature), such as proteins substantially homologous to the parent sequence. These modifications may be deliberate, as through site-directed mutagenesis, or may be accidental, such as through naturally occurring mutational events. All of these modifications are encompassed in the present invention so long as the modified E1 and E2 polypeptides function for their intended purpose. Thus, for example, if the E1 and/or E2 polypeptides are to be used in vaccine compositions, the modifications must be such that immunological activity (i.e., the ability to elicit a humoral or cellular immune response to the polypeptide) is not lost. Generally, then, for purposes of the present invention, the polypeptides will retain at least one T cell epitope such that a cellular immune response can be generated in a subject to which the polypeptides are delivered.

By "E1E2" or E1E2 protein complex is meant a protein containing at least one E1 polypeptide and at least one E2 polypeptide, as described above. Such a complex may also include all or a portion of the p7 region which occurs immediately adjacent to the C-terminus of E2. As shown in FIGS. 1 and 2A-2C, the p7 region is found at positions 747-809, numbered relative to the full-length HCV-1 polyprotein (amino acid positions 575-637 of SEQ ID NO:2). A representative E1E2 complex which includes the p7 protein is termed "E1E2$_{809}$" herein. The compositions comprising E1E2 protein complexes useful for practice of the invention can further include one or more adjuvants.

The mode of association of E1 and E2 in an E1E2 complex is immaterial. The E1 and E2 polypeptides may be associated through non-covalent interactions such as through electrostatic forces, or by covalent bonds. For example, the E1E2 polypeptides of the present invention may be in the form of a fusion protein which includes an immunogenic E1 polypeptide and an immunogenic E2 polypeptide, as defined above. The fusion may be expressed from a polynucleotide encoding an E1E2 chimera. Alternatively, E1E2 complexes may form spontaneously simply by mixing E1 and E2 proteins which have been produced individually. Similarly, when co-expressed and secreted into media, the E1 and E2 proteins can form a complex spontaneously. Thus, the term encompasses E1E2 complexes (also called aggregates) that spontaneously form upon purification of E1 and/or E2. Such aggregates may include one or more E1 monomers in association with one or more E2 monomers. The number of E1 and E2 monomers present need not be equal so long as at least one E1 monomer and one E2 monomer are present. Detection of the presence of an E1E2 complex is readily determined using standard protein detection techniques such as polyacrylamide gel electrophoresis and immunological techniques such as immunoprecipitation.

The terms "analog" and "mutein" refer to biologically active derivatives of the reference molecule, such as E1E2$_{809}$, or fragments of such derivatives, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"). Preferably, the analog or mutein has at least the same immunoreactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest, such as an E1E2 polypeptide, may include up to about 5-10 conservative or non-conservative amino acid substitutions, or even up to about 15-25 or 50 conservative or non-conservative amino acid substitutions, or any integer between 5-50, so long as the desired function of the molecule remains intact. One of skill in the art can readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion an N-terminal deletion, and/or an internal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein. For a description of known immunogenic fragments of HCV E1 and E2, see, e.g., Chien et al., International Publication No. WO 93/00365.

The term "epitope" as used herein refers to a sequence of at least about 3 to 5, preferably about 5 to 10 or 15, and not more than about 500 amino acids (or any integer therebetween), which define a sequence that by itself or as part of a larger sequence, elicits an immunological response in the subject to which it is administered. Often, an epitope will bind to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715. Using such techniques, a number of epitopes of HCV have been identified. See, e.g., Chien et al., *Viral Hepatitis and Liver Disease* (1994) pp. 320-324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope defining sequence can be subject to wide variations as these epitopes are believed to be formed by the three-dimensional shape of the antigen (e.g., folding). Thus, amino acids defining the epitope can be relatively few in number, but widely dispersed along the length of the molecule (or even on different molecules in the case of dimers, etc.), being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest. Conformational epitopes derived from the E1 and E2 regions are described in, e.g., International Publication No. WO 94/01778.

As used herein the term "T-cell epitope" refers to a feature of a peptide structure which is capable of inducing T-cell immunity towards the peptide structure or an associated hapten. T-cell epitopes generally comprise linear peptide determinants that assume extended conformations within the peptide-binding cleft of MHC molecules, (Unanue et al., *Science* (1987) 236:551-557). Conversion of polypeptides to MHC class II-associated linear peptide determinants (generally between 5-14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc, ed. G. C. Woodrow et al., (1990) pp. 109-116) and further that the amphipathic structures have an α-helical configuration (see, e.g., Spouge et al., *J. Immunol.* (1987) 138:204-212; Berkower et al., *J. Immunol.* (1986) 136:2498-2503).

Hence, segments of proteins that include T-cell epitopes can be readily predicted using numerous computer programs. (See e.g., Margalit et al., *Computer Prediction of T-cell Epitopes, New Generation Vaccines* Marcel-Dekker, Inc, ed. G. C. Woodrow et al., (1990) pp. 109-116). Such programs generally compare the amino acid sequence of a peptide to sequences known to induce a T-cell response, and search for patterns of amino acids which are believed to be required for a T-cell epitope.

An "immunological response" to an HCV antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays; CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376.

Thus, an immunological response as used herein may be one which stimulates the production of CTLs, and/or the production or activation of helper T cells. The antigen of interest may also elicit an antibody-mediated immune response, including, or example, neutralization of binding (NOB) antibodies. The presence of an NOB antibody response is readily determined by the techniques described in, e.g., Rosa et al., *Proc. Natl. Acad. Sci. USA* (1996) 93:1759. Hence, an immunological response may include one or more of the following effects: the production of antibodies by B-cells; and/or the activation of suppressor T-cells and/or γδT-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, 3, etc., of HCV which antigenic determinants are not necessarily identical due to sequence variation, but which occur in equivalent positions in the HCV sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived. Thus, a degenerate variant of $E1E2_{809}$ DNA is a molecule with one or more base differences in the DNA sequence from which the molecule is derived but that encodes the same $E1E2_{809}$ amino acid sequence.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence. FOR E1/E2, no stop start codons naturally occur in the polyprotein. Synthetic protein expression constructs can be made which comprise E1/E2 fusion proteins further comprising a start codon and optionally a secretory or leader sequence using various techniques known to the skilled artisan and an example of which is provided herein.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and synthetic DNA sequences. The term also captures sequences that include any of the known base analogs of DNA and RNA.

An "HCV polynucleotide" is a polynucleotide that encodes an HCV polypeptide, as defined above.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transformation, see further below. The exogenous polynucleotide may be maintained as a nonintegrated vector, for example, an episome, or alternatively, may be integrated into the host genome.

By "nucleic acid immunization" is meant the introduction of a nucleic acid molecule encoding one or more selected immunogens, such as an E1E2 complex, into a host cell, for the in vivo expression of the immunogen. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the immunogen encoded by the nucleic acid molecule.

The term "alphavirus" has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus (SIN), South African Arbovirus No. 86 (S.A.AR86), Girdwood S. A. virus, Ockelbo virus, Semliki Forest virus, Middelburg virus, Chikungunya virus, O'Nyong-Nyong virus, Ross River virus, Barmah Forest virus, Getah virus, Saglyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus. Preferred alphaviruses for use in the present invention are SIN strains, VEE strains, Ockelbo virus, and chimeric viruses thereof.

A "viral vector" refers to a nucleic acid construct that carries, and within certain embodiments, is capable of directing the expression of a nucleic acid molecule of interest, such as a polynucleotide encoding an E1E2 complex. Viral vectors may be utilized in several formats, including DNA, RNA, and recombinant replicon particles. Thus, as used herein, the term viral vector includes a nucleic acid provided in a viral particle, such as for example a defective chimeric alphavirus particle.

An “alphavirus vector” refers to a nucleic acid construct that carries, and within certain embodiments, is capable of directing the expression of a nucleic acid molecule of interest, such as a polynucleotide encoding an E1E2 complex. Alphavirus vectors may be utilized in several formats, including DNA, RNA, and recombinant replicon particles. Such replicon vectors have been derived from alphaviruses that include, for example, Sindbis virus, Semliki Forest virus, and/or Venezuelan equine encephalitis virus. See, e.g., U.S. Pat. Nos. 5,789,245; 5,814,482; and 6,376,235 and WO 02/099035, incorporated herein by reference in their entireties.

The terms “alphavirus RNA replicon vector”, “RNA replicon vector”, “replicon vector” or “replicon” refer to an RNA molecule that is capable of directing its own amplification or self-replication in vivo, within a target cell. To direct its own amplification, the RNA molecule should encode the polymerase(s) necessary to catalyze RNA amplification (e.g., alphavirus nonstructural proteins nsP1, nsP2, nsP3, nsP4) and also contain cis RNA sequences required for replication which are recognized and utilized by the encoded polymerase(s). An alphavirus RNA vector replicon typically contains the following ordered elements: 5' viral or cellular sequences required for nonstructural protein-mediated amplification (may also be referred to as 5' CSE, or 5' cis replication sequence, or 5' viral sequences required in cis for replication, or 5' sequence which is capable of initiating transcription of an alphavirus), sequences which, when expressed, code for biologically active alphavirus nonstructural proteins (e.g., nsP1, nsP2, nsP3, nsP4), and 3' viral or cellular sequences required for nonstructural protein-mediated amplification (may also be referred as 3' CSE, or 3' viral sequences required in cis for replication, or an alphavirus RNA polymerase recognition sequence). The alphavirus RNA vector replicon also should contain a means to express one or more heterologous sequence(s), such as for example, an IRES or a viral (e.g., alphaviral) subgenomic promoter (e.g., junction region promoter) which may, in certain embodiments, be modified in order to increase or reduce viral transcription of the subgenomic fragment, or to decrease homology with defective helper or structural protein expression cassettes, and one or more heterologous sequence(s) to be expressed. When used as vectors, the replicons will also contain additional sequences, for example, one or more heterologous sequence(s) encoding one or more polypeptides (e.g., a protein-encoding gene or a 3' proximal gene) and/or a polyadenylate tract.

As used herein, the terms "chimeric alphavirus particle" and "chimeric alphavirus replicon particle" refer to a chimera or chimeric particle such as a virus, or virus-like particle, specifically modified or engineered to contain a nucleic acid derived from a alphavirus other than the alphavirus from which either the capsid and/or envelope glycoprotein was derived (e.g., from a different virus). In such a particle, the nucleic acid derived from an alphavirus is an RNA molecule comprising one of any number of different lengths, including, but not limited to genome-length (encoding nonstructural and structural proteins) and replicon-length (deleted of one or more structural proteins). For example, and not intended as a limitation, chimeric replicon particles may include Sindbis virus (SIN) replicon RNA within a capsid having a Sindbis virus RNA binding domain and a Venezuelan equine encephalitis virus (VEE) envelope glycoprotein interaction domain, surrounded by a VEE glycoprotein envelope and/or a VEE replicon RNA having a deletion in nsP3, a SIN packaging signal inserted into the deletion in nsP3 and capsid and envelope proteins derived from SIN. Chimeric alphavirus vectors are described, for example, in U.S. Patent Publications 20030232324 and 20030148262, incorporated herein by reference in their entireties.

In a preferred embodiment, the invention employs defective alphavirus particles that are chimeric. As used herein, the term "defective alphavirus particle" refers to a virus particle that can generate copies of its RNA upon infection in a cell, thereby expressing any exogenous gene encoded on the alphavirus, but the virus is lacking in one or more functions required for production of new viral particles following infection. Typically, such defective alphavirus particles lack one or more structural genes required for generation of new particles. (See, e.g., WO/61772).

The terms "effective amount" or "pharmaceutically effective amount" of an immunogenic composition, as provided herein, refer to a nontoxic but sufficient amount of the composition to provide the desired response, such as an immunological response, and optionally, a corresponding therapeutic effect. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum chordata, including, without limitation, humans and other primates, including non-human primates such as chimpanzees and other apes and monkey species; farm animals such as cattle, sheep, pigs; goats and horses, domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

The term "treatment" as used herein refers to either (1) the prevention of infection or reinfection (prophylaxis), or (2) the reduction or elimination of symptoms of the disease of interest (therapy).

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that immunization methods using one or more initial administrations of HCV E1E2 protein complexes, followed by boosting with a viral vector comprising nucleic acid constructs encoding an HCV E1E2, results in enhanced HCV CD8+ T cell responses. Thus, as described in more detail below, subjects are initially administered E1E2 complexes, such as complexes expressed using $E1E2_{809}$ DNA, in one or more immunizations. The compositions including the E1E2 complexes may also contain adjuvants, such as submicron oil-in-water emulsions described in detail below. Subjects are subsequently boosted with a viral vector composition comprising nucleic acid constructs encoding E1E2 complexes, such as viral vector compositions containing alphavirus replicon particles encoding E1E2 complexes. The E1E2 complexes encoded by the nucleic acid constructs can be either the same E1E2 complex as used initially, or can encode other E1E2 proteins, as described further below, so long as an immune response is generated. Thus, for example, if complexes derived from $E1E2_{809}$ DNA are used to prime the immune response, the subject can be boosted with a composition including nucleic acid encoding $E1E2_{809}$, or nucleic acid encoding another E1E2 protein, such as $E1E2_{746}$. In a preferred embodiment, a viral vector as described herein is a defective alpahvirus particle, which can be a chimeric alphavirus particle.

Additionally, the compositions above can be used alone, or in combination with other compositions, such as compositions comprising other HCV proteins, compositions comprising DNA encoding other HCV proteins, as well as compositions comprising ancillary substances, such as immunoglobulins, cytokines, lymphokines, and chemokines, including but not limited to cytokines such as IL-1, IL-2, IL-4, IL-5, IL-6, IL-7, IL-12 etc. (see, e.g., International Publication No. WO 99/44636), modified IL-2 (cys 125→ser125), GM-CSF, M-CSF, tumor necrosis factor (TNF), interferons and pegylated interferons, such as γ-interferon, IP-10, MIP1β, FLP-3, ribavirin, RANTES, siRNA, antisense RNA, inhibitors of polymerase, helicase, GTPase, ATPase, protease, glycosylation, metalloprotease, and/or IRES. Thus, the present methods can be used with other therapeutic regimens for treating HCV infection. If used in combination with other compositions, such compositions can be administered prior to, concurrent with, or subsequent to the E1E2 compositions.

In order to further an understanding of the invention, a more detailed discussion is provided below regarding E1E2 protein and nucleic acid compositions, and additional compositions for use in the subject methods.

E1E2 Polypeptides

As explained above, in the methods of the invention, immune responses in subjects are primed using one or more administrations of compositions including E1E2 complexes. Subjects are then boosted using E1E2 nucleic acid constructs. E1, E2 and p7 are known to contain human T cell epitopes (both CD4+ and CD8+). E1E2 complexes comprise E1 and E2 polypeptides which include one or more T cell epitopes, associated either through non-covalent or covalent interactions. Moreover, multiple copies of specific, conserved T cell epitopes can be used in E1E2 complexes, such as a composite of epitopes from different genotypes.

The HCV E1 polypeptide is a glycoprotein and extends from approximately amino acid 192 to amino acid 383 (numbered relative to the polyprotein of HCV-1). See, Choo et al., *Proc. Natl. Acad. Sci. USA* (1991) 88:2451-2455. Amino acids at around 173 through approximately 191 represent a signal sequence for E1. An HCV E2 polypeptide is also a glycoprotein and extends from approximately amino acid 383 or 384 to amino acid 746. A signal peptide for E2 begins at approximately amino acid 364 of the polyprotein. Thus, the term "full-length" E1 or "not truncated" E1 as used herein refers to polypeptides that include, at least, amino acids 192-383 of an HCV polyprotein (numbered relative to HCV-1). With respect to E2, the term "full-length" or "not truncated" as used herein refers to polypeptides that include, at least, amino acids 383 or 384 to amino acid 746 of an HCV polyprotein (numbered relative to HCV-1). As will be evident from this disclosure, E1E2 polypeptides for use with the present invention may include additional amino acids from the p7 region, such as amino acids 747-809.

E2 exists as multiple species (Spaete et al., *Virol.* (1992) 188:819-830; Selby et al., *J. Virol* (1996) 70:5177-5182; Grakoui et al., *J. Virol.* (1993) 67:1385-1395; Tomei et al., *J. Virol.* (1993) 67:4017-4026) and clipping and proteolysis may occur at the N- and C-termini of the E1 and E2 polypeptides. Thus, an E2 polypeptide as found in an E1E2 complex may comprise at least amino acids 405-661, e.g., 400, 401, 402 ... to 661, such as 383 or 384-661, 383 or 384-715, 383 or 384-746, 383 or 384-749 or 383 or 384-809, or 383 or 384 to any C-terminus between 661-809, of an HCV polyprotein, numbered relative to the full-length HCV-1 polyprotein. Similarly, preferable E1 polypeptides for use herein can comprise amino acids 192-326, 192-330, 192-333, 192-360, 192-363, 192-383, or 192 to any C-terminus between 326-383, of an HCV polyprotein.

The E1E2 complexes may also be made up of immunogenic fragments of E1 and E2 which comprise epitopes, preferably T cell epitopes. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers. The E1 and E2 polypeptides may be from the same or different HCV strains.

For example, epitopes derived from, e.g., the hypervariable region of E2, such as a region spanning amino acids 384-410 or 390-410, can be included in the E2 polypeptide. A particularly effective E2 epitope to incorporate into the E2 sequence is one which includes a consensus sequence derived from this region, such as the consensus sequence Gly-Ser-Ala-Ala-Arg-Thr-Thr-Ser-Gly-Phe-Val-Ser-Leu-Phe-Ala-Pro-Gly-Ala-Lys-Gln-Asn (SEQ ID NO:3), which represents a consensus sequence for amino acids 390-410 of the HCV type 1 genome. Additional epitopes of E1 and E2 are known and described in, e.g., Chien et al., International Publication No. WO 93/00365.

Moreover, the E1 and E2 polypeptides of the complex may lack all or a portion of the membrane spanning domain. The membrane anchor sequence functions to associate the polypeptide to the endoplasmic reticulum. Normally, such polypeptides are capable of secretion into growth medium in which an organism expressing the protein is cultured. However, as described in International Publication No. WO 98/50556, such polypeptides may also be recovered intracellularly. Secretion into growth medium is readily determined using a number of detection techniques, including, e.g., polyacrylamide gel electrophoresis and the like, and immunological techniques such as immunoprecipitation assays as described in, e.g., International Publication No. WO 96/04301, published Feb. 15, 1996. With E1, generally polypeptides terminating with about amino acid position 370 and higher (based on the numbering of HCV-1 E1) will be retained by the ER and hence not secreted into growth media. With E2, polypeptides terminating with about amino acid position 731 and higher (also based on the numbering of the HCV-1 E2 sequence) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acids 730 and lower, are intended to be captured by the present invention. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond about amino acid position 715. Particularly preferred E2 truncations are those molecules truncated after any of amino acids 715-730, such as 725. If truncated molecules are used, it is preferable to use E1 and E2 molecules that are both truncated.

The E1 and E2 polypeptides and complexes thereof may also be present as asialoglycoproteins. Such asialoglycoproteins are produced by methods known in the art, such as by using cells in which terminal glycosylation is blocked. When these proteins are expressed in such cells and isolated by GNA lectin affinity chromatography, the E1 and E2 proteins aggregate spontaneously. Detailed methods for producing these E1E2 aggregates are described in, e.g., U.S. Pat. No. 6,074,852.

Moreover, the E1E2 complexes may comprise a heterogeneous mixture of molecules, due to clipping and proteolytic cleavage, as described above. Thus, a composition including E1E2 complexes may include multiple species of E1E2, such as E1E2 terminating at amino acid 746 ($E1E2_{746}$), E1E2 terminating at amino acid 809 ($E1E2_{809}$), or any of the other various E1 and E2 molecules described above, such as E2 molecules with N-terminal truncations of from 1-20 amino acids, such as E2 species beginning at amino acid 387; amino acid 402, amino acid 403, etc.

It should be noted that for convenience, the E1 and E2 regions are generally defined with respect to the amino acid number relative to the polyprotein encoded by the genome of HCV-1a, as described in Choo et al. (1991) *Proc Natl Acad Sci USA* 88:2451, with the initiator methionine being designated position 1. However, the polypeptides for use with the present invention are not limited to those derived from the HCV-1a sequence. Any strain or isolate of HCV can serve as the basis for providing immunogenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al. (1989) *Japan. Nucl. Acids Res.* 17:10367-10372; Takeuchi et al. (1990) *Gene* 91:287-291; Takeuchi et al. (1990) *J. Gen. Virol.* 71:3027-3033; and Takeuchi et al. (1990) *Nucl. Acids Res.* 18:4626. The complete coding sequences of two independent isolates, HCV-1 and BK, are described by Kato et al., (1990) *Proc. Natl. Acad. Sci. USA* 87:9524-9528 and Takamizawa et al., (1991) *J. Virol.* 65:1105-1113, respectively. HCV-1 isolates are described by Choo et al. (1990) *Brit. Med. Bull.* 46:423-441; Choo et al. (1991) *Proc. Natl. Acad. Sci. USA* 88:2451-2455 and Han et al. (1991) *Proc. Natl. Acad. Sci. USA* 88:1711-1715. HCV isolates HC-J1 and HC-J4 are described in Okamoto et al. (1991) *Japan J. Exp. Med.* 60:167-177. HCV isolates HCT 18, HCT 23, Th, HCT 27, EC1 and EC10 are described in Weiner et al. (1991) *Virol.* 180:842-848. HCV isolates Pt-1, HCV-K1 and HCV-K2 are described in Enomoto et al. (1990) *Biochem. Biophys. Res. Commun.* 170:1021-1025. HCV isolates A, C, D & E are described in Tsukiyama-Kohara et al. (1991) *Virus Genes* 5:243-254. HCV E1E2 polynucleotides and polypeptides for use in the compositions and methods of the invention can be obtained from any of the above cited strains of HCV or from newly discovered isolates isolated from tissues or fluids of infected patients.

E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes for use with the present invention may be expressed as a fusion protein wherein the desired portion of E1 is fused to the desired portion of E2.

Methods for producing E1E2 complexes from full-length, truncated E1 and E2 proteins which are secreted into media, as well as intracellularly produced truncated proteins, are known in the art. For example, such complexes may be produced recombinantly, as described in U.S. Pat. No. 6,121,020; Ralston et al., *J. Virol.* (1993) 67:6753-6761, Grakoui et al., *J. Virol.* (1993) 67:1385-1395; and Lanford et al., *Virology* (1993) 197:225-235.

Nucleic Acid Constructs Encoding the E1E2 Complexes

Polynucleotides encoding E1, E2 and E1E2 proteins contain less than an entire HCV genome and can be RNA or single- or double-stranded DNA. Preferably, the polynucleotides are isolated free of other components, such as proteins and lipids. The polynucleotides encode the E1 and E2 polypeptides and complexes thereof, described above, and thus comprise coding sequences thereof. Polynucleotides of the invention can also comprise other non-HCV nucleotide sequences, such as sequences coding for linkers, signal sequences, or ligands useful in protein purification such as glutathione-S-transferase and staphylococcal protein A.

Polynucleotides encoding the various HCV polypeptides can be isolated from a genomic library derived from nucleic acid sequences present in, for example, the plasma, serum, or liver homogenate of an HCV infected individual or can be synthesized in the laboratory, for example, using an automatic synthesizer. An amplification method such as PCR can be used to amplify polynucleotides from either HCV genomic DNA or cDNA encoding therefor.

Polynucleotides can comprise coding sequences for these polypeptides which occur naturally or can include artificial sequences which do not occur in nature. For example, it may be useful to provide an methionine start codon and leader sequence for the E1 E2 protein, since this protein is part of a larger fusion protein. These polynucleotides can be ligated to form a coding sequence for the E1E2 complexes using standard molecular biology techniques. If desired, polynucleotides can be cloned into an expression vector and transformed into, for example, bacterial, yeast, insect, or mammalian cells so that the fusion proteins of the invention can be expressed in and isolated from a cell culture.

The expression constructs of the present invention, encoding E1E2 proteins, or individual expression constructs comprising sequences encoding E1 and E2, may be used for nucleic acid immunization, in order to boost and stimulate an immunological response, such as a cellular immune response, using a viral vector that encodes and expresses the HCV E1/E2 proteins. In a preferred embodiment, the viral vector is a defective alpahvirus particle that is a chimeric alpahvirus particle.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:419-44198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., Biochem. Biophys. Res. Commun. (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219, 740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Venezuelan Equine Encephalitis virus (VEE), Sindbis virus (SIN) and Semliki Forest viruses, will also find use as viral vectors for delivering the gene of interest. Several members of the alphavirus genus have been developed as "replicon" expression vectors for use as vaccines and therapeutics. Replicon vectors may be utilized in several formats, including DNA and RNA, to make recombinant virus-like particles containing the replicon vectors (replicon particles). Such replicon vectors can be derived from any of the above-described alphaviruses, such as SIN (Xiong et al. (1989) *Science* 243:1188-1191; Dubensky et al., (1996) *J. Virol.* 70:508-519; Hariharan et al. (1998) *J. Virol.* 72:950-958; Polo et al. (1999) *PNAS* 96:4598-4603), Semliki Forest virus (Liljestrom (1991) *Bio/Technology* 9:1356-1361; Berglund et al. (1998) *Nat. Biotech.* 16:562-565), and VEE (Pushko et al. (1997) *Virology* 239:389-401). See, also, U.S. Pat. Nos. 5,789,245; 5,814,482; and 6,376,235 and WO 02/099035, incorporated herein by reference in their entireties.

The general strategy for construction of alphavirus-based expression vectors involves substituting the viral structural protein genes with the heterologous gene of interest, maintaining transcriptional control via the highly active subgenomic RNA promoter. Vectors of this configuration are termed RNA "replicons" and may be transcribed in vitro from cDNA using a bacteriophage promoter, or, generated in vivo directly from DNA when linked to a eukaryotic promoter. Alphavirus replicon RNA is generally packaged into recombinant vector particles by transient co-transfection with in vitro transcribed defective helper RNA, or, using stable packaging cell lines having structural protein expression cassettes. The structural protein expression cassette(s), also called "defective helper" constructs when they are incapable of replication on their own, used for vector packaging encode either the intact "native" alphavirus structural polyprotein that is post-translationally processed into mature C, E2, and E1; or, alphavirus structural proteins that have been split into separate cassettes encoding either C or E2/E1. See, e.g., U.S. Pat. Nos. 6,465,634; 6,426,196; 6,376,236; 6,342,372; 6,329,201; 6,015,686; 5,843,723; and International Publication Nos. WO 95/07995 and WO 96/17072, all of which are incorporated herein by reference in their entireties; Polo et al. (1999) *Proc. Nat'l Acad Sci USA* 96:4598-4603; Dubensky et al. (1996) *J. Virology* 70(1):508-519; Frolov et al. (1996). *Proc Natl Acad Sci USA.* 93(21):11371-11377).

Particularly preferred for use in delivering the E1E2 boost, is a chimeric alphavirus vector, such as replicon particle chimeras of SIN and VEE. Chimeric alphavirus vectors are described, for example, in U.S. Patent Publications 20030232324 and 20030148262, incorporated herein by reference in its entirety, and Perri et al., *J. Virol.* (2003) 77:10394-10403. For example, particles with VEE-E1E2 replicon RNA packaged within SIN envelope glycoproteins or SIN-E1E2 replicon RNA within VEE envelope glycoproteins will find use with the present methods. As shown in the examples below, VEE/SIN replicon particles induced HCV-specific CD8+ T cell responses in murine models when administered after priming with E1E2 protein vaccines.

Other vectors can be used, including but not limited to simian virus 40 and cytomegalovirus. Bacterial vectors, such as *Salmonella* ssp. *Yersinia enterocolitica, Shigella* spp., *Vibrio cholerae, Mycobacterium* strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

One preferred method for adsorbing macromolecules onto prepared microparticles is described in International Publication No. WO 00/050006, incorporated herein by reference in its entirety. Briefly, microparticles are rehydrated and dispersed to an essentially monomeric suspension of microparticles using dialyzable anionic or cationic detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methyl-glucamide (MEGA-10); cholic acid; sodium cholate; deoxycholic acid; sodium deoxycholate; taurocholic acid; sodium taurocholate; taurodeoxycholic acid; sodium taurodeoxycholate; 3-[(3-cholamidopropyl)dimethylamonio]-1-propane-sulfonate (CHAPS); 3-[(3-cholamidopropyl)dimethylammonio]-2-hydroxy-1-propane-sulfonate (CHAPSO); -dodecyl-N,N-dimethyl-3-ammonio-1-propane-sulfonate (ZWITTERGENT 3-12); N,N-bis-(3-D-gluconeamidopropyl)-deoxycholamide (DEOXYBIGCHAP); -octylglucoside; sucrose monolaurate; glycocholic acid/sodium glycocholate; laurosarcoine (sodium salt); glycodeoxycholic acid/sodium glycodeoxycholate; sodium dodceyl sulfate (SDS); 3-(trimethylsilyl)-1-propanesulfonic acid (DSS); cetrimide (CTAB, the principal component of which is hexadecyltrimethylammonium bromide); hexadecyltrimethylammonium bromide; dodecyltrimethylammonium bromide; hexadecyltrimethyl-ammonium bromide; tetradecyltrimethylammonium bromide; benzyl dimethyldodecylammonium bromide; benzyl dimethylhexadecylammonium chloride; and benzyl dimethyltetradecylammonium bromide. The above detergents are commercially available from e.g., Sigma Chemical Co., St. Louis, Mo. Various cationic lipids known in the art can also be used as detergents. See Balasubramaniam et al., 1996, *Gene Ther.,* 3:163-72 and Gao, X., and L. Huang. 1995, *Gene Ther.,* 2:7110-722.

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451,002, 6,418,341, 6,233,483, U.S. Patent Publication No. 2002/0146831; and International Publication No. WO/0045823, all of which are incorporated herein by reference in their entireties.

Moreover, the HCV polynucleotides can be adsorbed to, or entrapped within, an ISCOM. Classic ISCOMs are formed by combination of cholesterol, saponin, phospholipid, and immunogens, such as viral envelope proteins. Generally, the HCV molecules (usually with a hydrophobic region) are solubilized in detergent and added to the reaction mixture, whereby ISCOMs are formed with the HCV molecule incorporated therein. ISCOMS are also referred to herein as IMX. ISCOM matrix compositions are formed identically, but without viral proteins. Proteins with high positive charge may be electrostatically bound in the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998); U.S. Pat. Nos. 4,981,684, 5,178,860, 5,679,354 and 6,027,732, incorporated herein by reference in their entireties; European Publ. Nos. EPA 109,942; 180,564 and 231,039; and Coulter et al. (1998) *Vaccine* 16:1243.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Other HCV Polypeptides and Polynucleotides

As explained above, the methods of the present invention may employ other compositions comprising HCV immunogens or DNA encoding such immunogens. Such compositions can be delivered prior to, subsequent to, or concurrent with the E1E2 complex compositions, as well as prior to, subsequent to, or concurrent with E1E2 nucleic acid compositions for boosting the immune response.

The methods of the present invention may also employ other HCV proteins in place of the E1/E2 as antigen for priming and boosting the immune response to HCV. IN some embodiments, the invention may employ non-structural (NS) proteins from HCV fused to one or more structural proteins of HCV such as E1, E2 and or core protean. In one embodiment, the invention provides a priming protein composition comprising an HCV fusion protein consisting essentially of an E2

The genome of the hepatitis C virus typically contains a single open reading frame of approximately 9,600 nucleotides, which is transcribed into a polyprotein. The full-length sequence of the polyprotein is disclosed in European Publication No. 388,232 and U.S. Pat. No. 6,150,087. As shown in Table 1 and FIG. 1, An HCV polyprotein, upon cleavage, produces at least ten distinct products, in the order of $NH_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) *Proc. Natl. Acad. Sci. USA* 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, either alone or in combination with NS3 (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. Completion of polyprotein maturation is initiated by autocatalytic cleavage at the NS3-NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658-1711), two proteins (NS4b found at about positions. 1712-1972, and NS5a found at about positions 1973-2420), and an RNA-dependent RNA polymerase (NS5b found at about positions 2421-3011).

TABLE 1

| Domain | Approximate Boundaries* |
| --- | --- |
| C (core) | 1-191 |
| E1 | 192-383 |

TABLE 1-continued

| Domain | Approximate Boundaries* |
|---|---|
| E2 | 384-746 |
| P7 | 747-809 |
| NS2 | 810-1026 |
| NS3 | 1027-1657 |
| NS4a | 1658-1711 |
| NS4b | 1712-1972 |
| NS5a | 1973-2420 |
| NS5b | 2421-3011 |

*Numbered relative to HCV-1. See, Choo et al. (1991) Proc. Natl. Acad. Sci. USA 88: 2451-2455. Unless otherwise indicated, all amino acid numbering of HCV constructs is relative to HCV-1.

Sequences for the above HCV polyprotein products, DNA encoding the same and immunogenic polypeptides derived therefrom; are known (see, e.g., U.S. Pat. No. 5,350,671). For example, a number of general and specific immunogenic polypeptides, derived from the HCV polyprotein, have been described. See, e.g., Houghton et al., European Publ. Nos. 318,216 and 388,232; Choo et al. *Science* (1989) 244:359-362; Kuo et al. *Science* (1989) 244:362-364; Houghton et al. *Hepatology* (1991) 14:381-388; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents.

Any desired immunogenic HCV polypeptide or DNA encoding the same can be utilized with the present invention. For example, HCV polypeptides derived from the Core region, such as polypeptides derived from the region found between amino acids 1-191; amino acids 10-53; amino acids 1045; amino acids 67-88; amino acids 86-100; 81-130; amino acids 121-135; amino acids 120-130; amino acids 121-170; and any of the Core epitopes identified in, e.g., Houghton et al., U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087, will find use with the subject methods.

Additionally, polypeptides derived from the nonstructural regions of the virus will also find use herein. The NS3/4a region of the HCV polyprotein has been described and the amino acid sequence and overall structure of the protein are disclosed in Yao et al. *Structure* (November 1999) 7:1353-1363. See, also, Dasmahapatra et al., U.S. Pat. No. 5,843,752. As explained above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Moreover, polypeptides for use in the subject compositions and methods may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are useful in the present methods and are known in the art and described in, e.g., Houghton et al, U.S. Pat. No. 5,350,671; Chien et al. *Proc. Natl. Acad. Sci. USA* (1992) 89:10011-10015; Chien et al. *J. Gastroent. Hepatol.* (1993) 8:S33-39; Chien et al., International Publ. No. WO 93/00365; Chien, D. Y., International Publ. No. WO 94/01778; and U.S. Pat. No. 6,150,087.

Additionally, multiple epitope fusion antigens (termed "MEFAs"), as described in, e.g., U.S. Pat. Nos. 6,514,731 and 6,428,792, may be used in the present methods. Such MEFAs include multiple epitopes derived from two or more of the various viral regions. The epitopes are preferably from more than one HCV strain, thus providing the added ability to protect against multiple strains of HCV in a single vaccine.

As explained above, for convenience, the various HCV regions have been defined with respect to the amino acid number relative to the polyprotein encoded by the genome of HCV-1a, as described in Choo et al. (1991) *Proc Natl Acad Sci USA* 88:2451, with the initiator methionine being designated position 1. However, HCV polypeptides and polynucleotides for use with the present invention are not limited to those derived from the HCV-1a sequence and any strain or isolate of HCV can serve as the basis for providing antigenic sequences for use with the invention, as explained in detail above.

The above polynucleotides and polypeptides can be obtained using the methods of recombinant production described above for E1E2 polypeptides and polynucleotides.

Immunogenic Compositions

Once produced, the E1E2 polynucleotides, complexes or other immunogens may be provided in immunogenic compositions, in e.g., prophylactic (i.e., to prevent infection) or therapeutic (to treat HCV following infection) vaccine compositions. The compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present, e.g., in protein compositions used to prime the immune response to E1E2. Carriers are molecules that do not themselves induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the immunogenic polypeptide may be conjugated to a bacterial toxoid, such as toxoid from diphtheria, tetanus, cholera, etc.

Adjuvants may also be present in the compositions to enhance the immune response. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose. In one embodiment the aluminum based adjuvant for use in the present invention is alum (aluminum potassium sulfate (AlK(SO$_4$)$_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant (Al(OH)$_3$) or crystalline aluminum oxyhydroxide (AlOOH), which is an excellent adsorbant, having a surface area of approximately 500 m$^2$/g. Alternatively, aluminum phosphate adjuvant (AlPO$_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837; and U.S. Pat. Nos. 6,299,884 and 6,451, 325, incorporated herein by reference in their entireties. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:423-44237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilar ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338; and Gerber et al., "Human Papillomavirus Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Adjuvants suitable for use in the invention include bacterial or microbial derivatives such as:

(1) Non-toxic derivatives of enterobacterial lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 13 (part 3):664-658; Bhagat et al., "CpG penta- and hexadeoxyribonucleotides as potent immunomodulatory agents" BBRC (2003) 300:853-861 and WO03/035836.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references; Beignon, et al., "The LTR72 Mutant of Heat-Labile Enterotoxin of *Escherichia coli* Enhances the Ability of Peptide Antigens to Elicit CD4+ T Cells and Secrete Gamma Interferon after Co application onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol. (2000) 290(4-5):455-461; Scharton-Kersten et al., "Transcutaneous Immunization with Bacterial ADP-Ribosylating Exotoxins, Subunits and Unrelated-Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167.

F. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethyl-cellulose. Chitosan and derivatives thereof may also be used as adjuvants in the invention. E.g. WO99/27960.

G. Microparticles

Microparticles may also be used as adjuvants in the invention. Microparticles (i.e. a particle of ~100 nm to ~150 µm in diameter, more preferably ~200 nm to ~30 µn in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds.

Examples of imidazoquinoline compounds suitable for use adjuvants in the invention include Imiquimod and its analogues, described further in Stanley, "Imiquimod and the imidazoquinolines: mechanism of action and therapeutic potential" Clin Exp Dermatol (2002) 27(7):571-577; Jones; "Resiquimod 3M", Curr Opin Investig Drugs (2003) 4(2): 214-218; and U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612.

M. Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/ or oil-in-water emulsions (See European patent applications 0835318, 0735898 and 0761231);

(6) SAF, containing 10% Squalane, 0.40/9 Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines. The contents of all of the above cited patents, patent applications and journal articles are incorporated by reference as if set forth fully herein.

Compositions for use in the invention will comprise a therapeutically effective amount of DNA encoding the E1E2 complexes (or a therapeutically effective amount of protein) and any other of the above-mentioned components, as needed. By "therapeutically effective amount" is meant an amount of an protein or DNA encoding the same which will induce an immunological response, preferably a protective immunological response, in the individual to which it is administered. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

E1E2 protein compositions can comprise mixtures of one or more of the E1E2 complexes, such as E1E2 complexes derived from more than one viral isolate, as well as additional HCV antigens. Moreover, as explained above, the E1E2 complexes may be present as a heterogeneous mixture of molecules, due to clipping and proteolytic cleavage. Thus, a composition including E1E2 complexes may include multiple species of E1E2, such as E1E2 terminating at amino acid 746 ($E1E2_{746}$), E1E2 terminating at amino acid 809 ($E E2_{809}$), or any of the other various E1 and E2 molecules described above, such as E2 molecules with N-terminal truncations of from 1-20 amino acids, such as E2 species beginning at amino acid 387, amino acid 402, amino acid 403, etc.

As explained above, the compositions (both DNA and protein) may be administered in conjunction with other antigens and immunoregulatory agents, such as immunoglobulins, cytokines, lymphokines, and chemokines, including but not limited to cytokines such as IL-1, IL-2, IL-4, IL-5, IL-6, IL-7, IL-12 etc. (see, e.g., International Publication No. WO 99/44636), modified IL-2 (cys125→ser125), GM-CSF, M-CSF, tumor necrosis factor (TNF), interferons and pegylated interferons, such as γ-interferon, IP-10, MIP1β, FLP-3, ribavirin, RANTES, SiRNA, antisense RNA, inhibitors of polymerase, helicase, GTPase, ATPase, protease, glycosylation, metalloprotease, and/or IRES. Thus, the present methods can be used with other therapeutic regimens for treating HCV infection. If used in combination with other compositions, such compositions can be administered prior to, concurrent with, or subsequent to the E1E2 compositions.

HCV-Specific T Cells

HCV-specific T cells that are activated by the above-described E1E2 complexes expressed in vivo or in vitro, preferably recognize an epitope of an HCV polypeptide such as an E1 and/or E2 polypeptide, or an E1E2 complex. HCV-specific T cells can be $CD8^+$ or $CD4^+$.

HCV-specific $CD8^+$ T cells preferably are cytotoxic T lymphocytes (CTL) which can kill HCV-infected cells that display E1 and/or E2 epitopes complexed with an MHC class I molecule. HCV-specific $CD8^+$ T cells may also express interferon-γ (IFN-γ). HCV-specific $CD8^+$ T cells can be detected by, for example, $^{51}Cr$ release assays (see the examples). $^{51}Cr$ release assays measure the ability of HCV-specific $CD8^+$ T cells to lyse target cells displaying an E1, E2 or E1E2 epitope. HCV-specific $CD8^+$ T cells which express IFN-γ can also be detected by immunological methods, preferably by intracellular staining for IFN-γ after in vitro stimulation with an E1, E2 or E1E2 polypeptide (see the examples).

HCV-specific $CD4^+$ cells activated by the above-described E1E2 complexes, expressed in vivo or in vitro, preferably recognize an epitope of an E1 and/or E2 polypeptide, including an epitope of an E1E2 complex, that is bound to an MHC class II molecule on an HCV-infected cell and proliferate in response to stimulating with E1E2 complexes.

HCV-specific $CD4^+$ T cells can be detected by a lymphoproliferation assay (see examples). Lymphoproliferation assays measure the ability of HCV-specific $CD4^+$ T cells to proliferate in response to an E1, E2 and/or E1E2 epitope.

Methods of Activating HCV-Specific T Cells

The E1E2 proteins or polynucleotides can be used to stimulate an immune response, such as to activate HCV-specific T cells either in vitro or in vivo. Activation of HCV-specific T cells can be used, inter alia, to provide model systems to optimize CTL responses to HCV and to provide prophylactic or therapeutic treatment against HCV infection. For in vitro activation, proteins are preferably supplied to T cells via a plasmid or a viral vector, such as an alphavirus vector, as described above.

Polyclonal populations of T cells can be derived from the blood, and preferably from peripheral lymphoid organs, such as lymph nodes, spleen, or thymus, of mammals that have been infected with an HCV. Preferred mammals include mice, chimpanzees, baboons, and humans. The HCV serves to expand the number of activated HCV-specific T cells in the mammal. The HCV-specific T cells derived from the mammal can then be restimulated in vitro by adding, e.g., HCV E1E2, to the T cells. The HCV-specific T cells can then be tested for, inter alia, proliferation, the production of IFN-γ, and the ability to lyse target cells displaying E1E2 epitopes in vitro.

In a lymphoproliferation assay, HCV-activated $CD4^+$ T cells proliferate when cultured with an E1E2 epitopic peptide, but not in the absence of an epitopic peptide. Thus, particular E1 and E2 epitopes or other HCV antigens that are recognized by HCV-specific $CD4^+$ T cells can be identified using a lymphoproliferation assay.

Similarly, detection of IFN-γ in HCV-specific $CD8^+$ T cells after in vitro stimulation with the above-described HCV proteins, can be used to identify E1, E2, and E1E2 epitopes or other HCV antigens that are particularly effective at stimulating $CD8^+$ T cells to produce IFN-γ (see examples).

Further, $^{51}Cr$ release assays are useful for determining the level of CTL response to HCV. See Cooper et al. Immunity 10:439-449. For example, HCV-specific $CD8^+$ T cells can be derived from the liver of an HCV infected mammal. These T cells can be tested in $^{51}Cr$ release assays against target cells displaying, e.g., E1E2 epitopes. Several target cell populations expressing different E1E2 epitopes can be constructed so that each target cell population displays different epitopes of E1E2. The HCV-specific $CD8^+$ cells can be assayed against each of these target cell populations. The results of the $^{51}$Cr release assays can be used to determine which epitopes of E1E2 are responsible for the strongest CTL response to HCV. E1E2 complexes which contain the epitopes responsible for the strongest CTL response can then be constructed using the information derived from the $^{51}$Cr release assays.

Administration

Typically, the immunogenic compositions (both DNA and protein) are prepared as injectables, either as liquid solutions or suspensions; solid forms suitable for solution in, or suspension in, liquid vehicles prior to injection may also be prepared. Thus, once formulated, the compositions are conventionally administered parenterally, e.g., by injection, either subcutaneously or intramuscularly. Additional formulations suitable for other modes of administration include oral and pulmonary formulations, suppositories, and transdermal applications.

Dosage treatment may be a single prime dosage and a single boost, or may be a multiple dose schedule. The interval between dosages (priming and boosting) will vary according to factors such as the age of the patient and the nature of the composition and these factors can be assessed by a physician. Administration of the first priming and boosting doses is generally separated by at least 2 weeks, typically at least 4 weeks. The methods of the invention may comprise more than one priming dose and/or more than one boosting dose, e.g., two, or more priming doses followed by two or more booster doses. The term "memory" boost refers to any boosting dose given after the initial boost. The time at which the "memory" boost is administered can vary from hours (e.g., 1 to 72 hours or any timepoint therebetween) or days (e.g, 1 to 90 days or any timepoint therebetween) to months (e.g., 1 to 36 months or any timepoint therebetween) or even years after the initial boost. More than one memory boost may be administered at the same or varying time intervals with respect to each other. Identical or different immunogenic compositions may be used for each priming dose. Priming and boosting doses may be therefore distinguished by the route of administration, rather than by their timing.

Preferably, the amount administered is sufficient to bring about treatment or prevention of disease symptoms. The exact amount necessary will vary depending on the subject being treated; the age and general condition of the individual to be treated; the capacity of the individual's immune system to engage in an immune response; the degree of protection desired; the severity of the condition being treated; the particular macromolecule selected and its mode of administration, among other factors. An appropriate effective amount can be readily determined by one of skill in the art. A "therapeutically effective amount" will fall in a relatively broad range that can be determined through routine trials using in vitro and in vivo models known in the art. The amount of E1E2 nucleic acid and polypeptides used in the examples below provides general guidance which can be used to optimize the elicitation of HCV-specific cellular immune responses, such as to activate HCV-specific T cells in vivo.

For example, the immunogen is preferably injected intramuscularly to a large mammal, such as a primate, for example, a baboon, chimpanzee, or human. For delivery of E1E2 protein, generally about 0.1 μg to about 5.0 mg of immunogen will be delivered per dose, or any amount between the stated ranges, such as 0.5 μg to about 10 mg, 1 μg to about 2 mg, 2.5 μg to about 250 μg, 4 μg to about 200 μg, such as 4, 5, 6, 7, 8, 9, 10 . . . 20 . . . 30 . . . 40 . . . 50 . . . 60 . . . 70 . . . 80 . . . 90 . . . 100, etc., μg per dose. For the booster administrations, the amount of E1E2 nucleic acid constructs delivered will depend on the vector, if any used. For example, if E1E2 DNA is delivered without a viral vector, about 1 μg to 500 mg of DNA, such as 5 μg to 100 mg of DNA, e.g., 10 μg to 50 mg, or 100 μg to 5 mg, such as 20 . . . 30 . . . 40 . . . 50 . . . 60 . . . 100 . . . 200 μg and so on, to 500 μg DNA, and any integer between the stated ranges, will find use in the subject methods. If viral vectors, such as alphavirus replicons, are used for delivery, generally, an effective dose will include on the order of from about $10^5$ to $10^{20}$ infectious units of the viral vectors, more preferably $10^8$ to $10^{15}$, and even more preferably about $10^{10}$ to $10^{13}$ infectious units of the viral vectors, or any value within these ranges.

The E1E2 nucleic acid constructs of the present invention are administered using standard gene delivery protocols. Methods for gene delivery are known in the art. See, e.g., U.S. Pat. Nos. 5,399,346, 5,580,859, 5,589,466. E1E2 nucleic acid constructs can be delivered either directly to the vertebrate subject or, alternatively, delivered ex vivo, to cells derived from the subject and the cells reimplanted in the subject.

Administration of the E1E2 polypeptides and nucleic acid can elicit a cellular immune response, and/or an anti-E1, anti-E2 and/or anti-E1E2 antibody titer in the mammal that lasts for at least 1 week, 2 weeks, 1 month, 2 months, 3 months, 4 months, 6 months, 1 year, or longer. As explained above, E1E2 nucleic acid can also be administered to provide a memory response. If such a response is achieved, antibody titers or the cellular immune response may decline over time, however exposure to the HCV virus or immunogen results in the rapid induction of antibodies and/or a cellular immune response, e.g., within only a few days. Optionally, such responses can be maintained in a mammal by providing one or more booster injections of the E1E2 nucleic acid constructs, as explained above, at 2 weeks, 1 month, 2 months, 3 months, 4 months, 5 months, 6 months, 1 year, or more after the primary injection.

A composition for use with the methods of the invention is administered in a manner compatible with the particular composition used and in an amount which is effective to stimulate an immune response, such as to activate HCV-specific T cells as measured by, inter alia, a $^{51}Cr$ release assay, a lymphoproliferation assay, or by intracellular staining for IFN-γ. The proteins and/or polynucleotides can be administered either to a mammal which is not infected with an HCV or can be administered to an HCV-infected mammal. An effective amount of the composition of the invention can be readily determined using only routine experimentation. In vitro and in vivo models described above can be employed to identify appropriate doses. The amount of protein and polynucleotide used in the example described below provides general guidance which can be used to optimize the activation of HCV-specific T cells either in vivo or in vitro.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Enzymes were purchased from commercial sources, and used according to the manufacturers' directions.

In the isolation of DNA fragments, except where noted, all DNA manipulations were done according to standard procedures. See, Sambrook et al., supra. Restriction enzymes, $T_4$ DNA ligase, *E. coli*, DNA polymerase II, Klenow fragment, and other biological reagents can be purchased from commercial suppliers and used according to the manufacturers' directions. Double stranded DNA fragments were separated on agarose gels.

Sources for chemical reagents generally include Sigma Chemical Company, St. Louis, Mo.; Alrich, Milwaukee, Wis.; Roche Molecular Biochemicals, Indianapolis, Ind.

Production of $E1E2_{809}$ Protein

The plasmid pCMVtpaE1E2p7 (6275 bp) was constructed by cloning HCV-1 encoding amino acids 192 to 809 with the upstream tissue plasminogen activator (tpa) signal sequence into the pnewCMV-II expression vector. The pnewCMV vector is a pUC19-based cloning vector comprising the following elements: an SV40 origin of replication, a human CMV enhancer/promoter, a human CMV intron, a human tissue plasminogen activator (tPA) leader, a bovine growth hormone poly A terminator and an ampicillin resistance gene.

$E1E2_{809}$ was expressed from recombinant CHO cells as described previously (Spaete et al., *Virology* (1992) 188:819-830). E1E2 complexes extracted from inside the CHO cells with Triton X-100 detergent. The E1E2 complexes were purified using *Galanthus nivalis* lectin agarose (Vector Laboratories, Burlingame, Calif.) chromatography and fast flow S-Sepharose cation-exchange chromatography (Pharmacia).

2 µg E1E2 complexes produced by expressing the $E1E2_{809}$ polynucleotides were emulsified with the submicron oil-in-water emulsion MF59. MF59 was manufactured at Chiron Vaccines, Marburg and has previously been described in detail (Ott et al., "MF59 Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296)

Alphaviruses Encoding $E1E2_{809}$

Replication-defective alphavirus particles represent an efficient vaccine delivery platform because of high-level expression of the foreign antigen, the lack of preexisting immunity in humans, the targeting of dendritic cells, and potent stimulation of innate immunity. In particular, VEE/SIN replicon particle chimeras were used that combine the selected desirable qualities of Sinbis virus (SIN) and Venezuelan equine encephalitis virus (VEE). Such chimeras were produced as described in Perri et al., *J. Virol.* (2003) 77:10394-10403 and Patent Publications 20030232324 and 20030148262, incorporated herein by reference in their entireties.

Cell Line Propagation and Infection

BHK-21 cells were maintained in Dulbecco minimum essential medium (DMEM) supplemented with 10% fetal calf serum (FCS), 10 mM sodium pyruvate, and penicillin and streptomycin at 37° C. with 5% $CO_2$. Cell monolayers of approximately 80% confluency were infected with replicon particles for 1 h in DMEM containing 1% FCS at 37° C. and then incubated overnight in DMEM containing 10% FCS.

Replicon Vector and Defective Helper Constructs

VCR-Chim2.1 was derived from VCR (Perri et al., *J. Virol.* 2003, 77:10394-403) by (i) inserting a PCR-amplified Sindbis virus (SIN) packaging sequence (nt 945 to 1076 of the SIN genome) as an in-frame fusion within the Venezuelan equine encephalitis virus (VEE) nonstructural protein gene 3 (nsP3) gene between the XhoI sites at nt 5493 and 5595 and (ii) replacing the VEE 3' untranslated region (3 UTR) with the SIN 3'UTR from the previously published SIN-derived replicon vector, SINCR (Perri et al., *J. Virol.* 2003, 77: 10394-403). E1E2 (746) and E1E2p7 (809) gene fragments for insertion into the chimeric vector were generated by PCR amplification of pCMVtpaE1E2p7, and then the cDNA were inserted into the VCR-Chim2.1 replicon vectors, resulting in constructs VEE/SIN-$E1E2_{746}$ and VEE/SIN-$E1E2_{809}$.

Production of Alphavirus Replicon Particles Expressing HCV Proteins

Sequences encoding either capsid or envelope glycoproteins from SIN were inserted into the VEE-based defective helper backbone (VCR-DH) (Perri et al., *J. Virol.* 2003, 77: 10394-403).

Chimeric replicon particles were generated by coelectroporation of in vitro-transcribed RNAs corresponding to a replicon and two defective helpers, one expressing capsid protein and the other expressing envelope glycoproteins, as previously described (Perri et al., *J. Virol.* 2003, 77: 10394-403).

Replicon particles expressing HCV-$E1E2_{746}$ or $E1E2_{809}$ were harvested as culture supernatants at 24 h postelectroporation, clarified by filtration, and purified by cation exchange chromatography. Replicon particle titers were determined by intracellular staining of expressed E1 and E2, following overnight infection of BHK-21 cells with serial dilutions of particles. Infected cells were permeabilized and fixed by using a Cytofix/Cytoperm kit (Pharmingen) and then stained with fluorescein isothiocyanate-conjugated antibodies to HCV E1 or E2 antigen. Using flow cytometry analysis, the percentage of E1 or E2-positive cells was determined and used to calculate titers. The absence of contaminating replication-competent virus was determined by five consecutive infections of naive BHK-21 cell and determination of titers. Finally, endotoxin levels were measured for all replicon particle samples and shown to be <0.5 endotoxin unit/ml.

NS Polyproteins

Epitopes recognized by a T-cell receptor on an HCV-activated T cell can also be identified by, for example, 5Cr release assay or by lymphoproliferation assay (see the examples). In a 5Cr release assay, target cells can be constructed that display the epitope of interest by cloning a polynucleotide encoding the epitope into an expression vector and transforming the expression vector into the target cells. HCV 30 specific CD8+ T cells will lyse target cells displaying, for example, an NS3, NS4, NS5a, NS5b, NS3NS4NS5a, or NS3NS4NS5aNS5b epitope and will not lyse cells that do not display such an epitope. In a lymphoproliferation assay, HCV-activated CD4+ T cells will proliferate when cultured with, for example, an NS3, NS4, NS5a, NS5b, NS3NS4NS5a, or NS3NS4NS5aNS5b epitopic peptide, but not in the absence of an HCV epitopic peptide.

Figure 7:
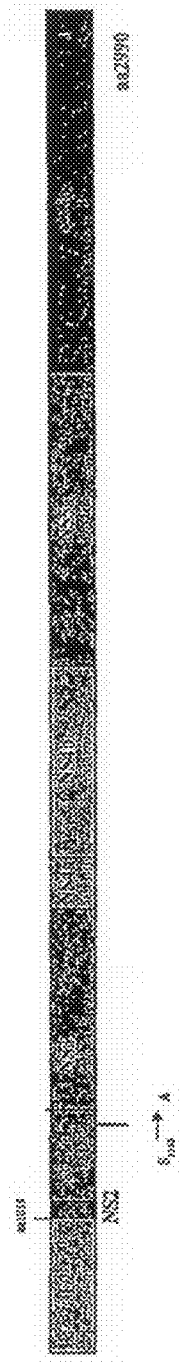
FIG. 7 shows a diagram of the E2NS3*NS4NS5tcore121 fusion protein as described in the examples.
Figure 8:
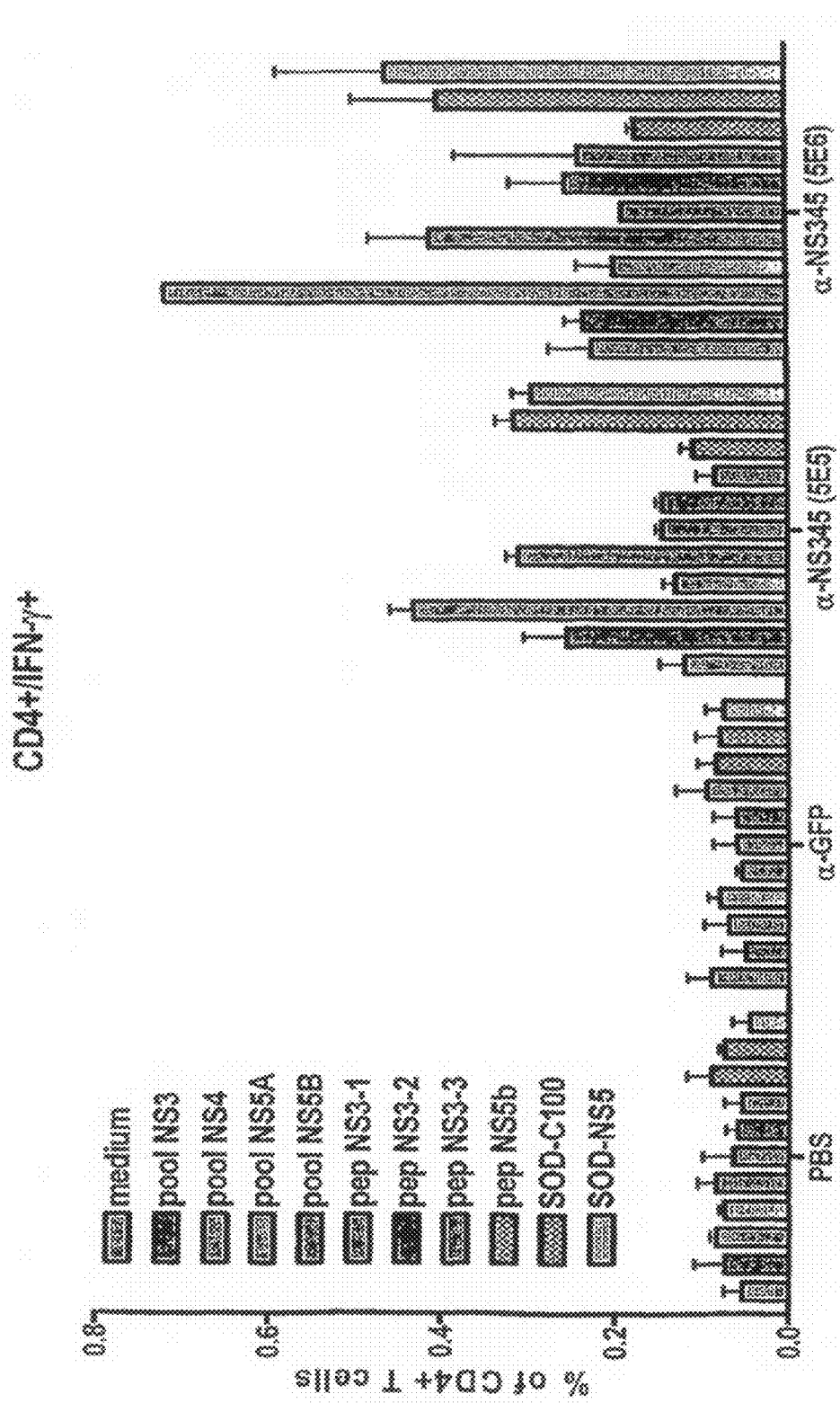
FIG. 8 shows graphically the results of CD4 HCV specific T cells generated following immunization with various NS alphavirus constructs as described in the examples.
Figure 9:
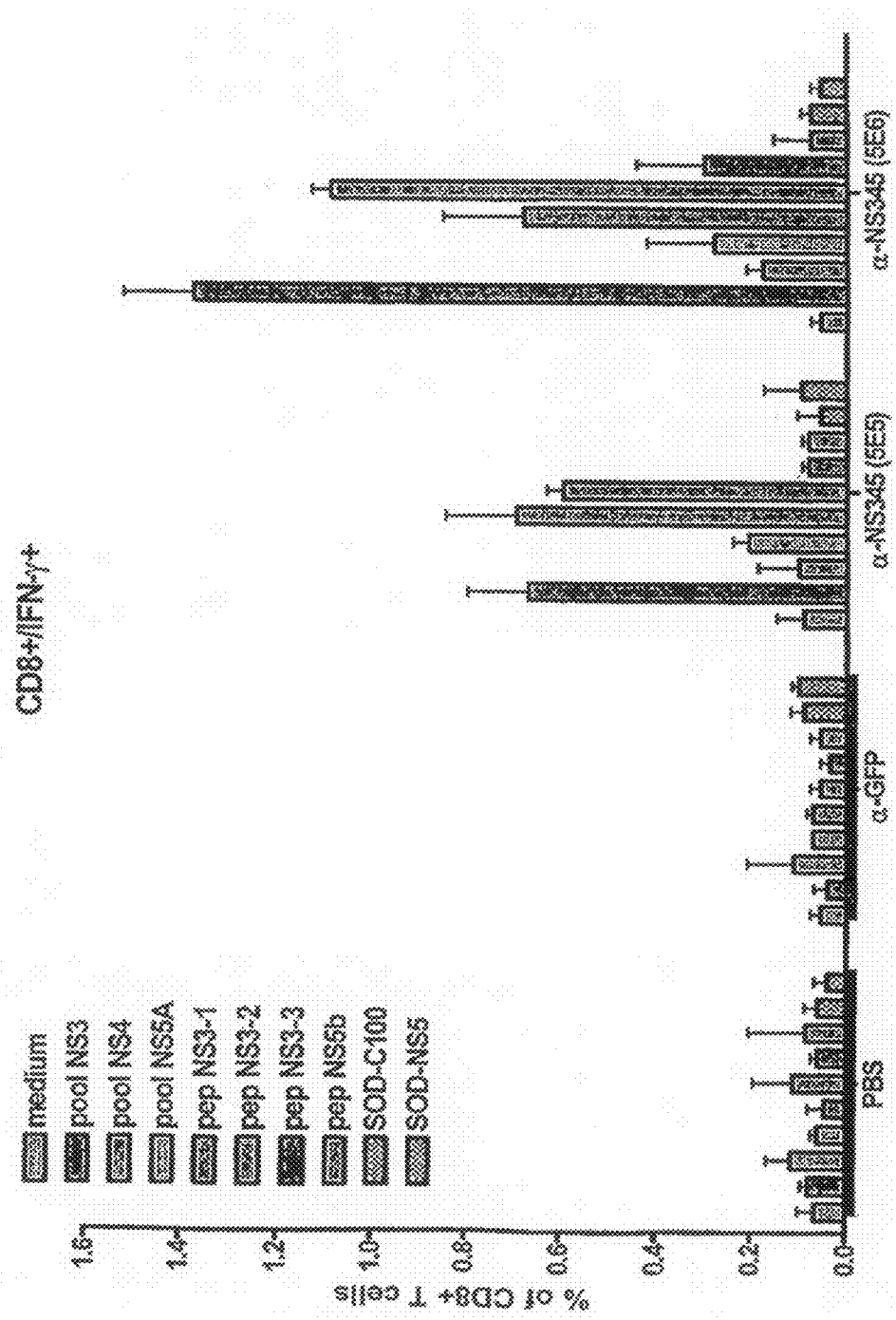
FIG. 9 shows graphically the results of CD8 HCV specific T cells generated following immunization with various NS alphavirus constructs as described in the examples.

E2, NS3, NS4, NS5a, and NS5b polypeptides can occur in any order in the fusion protein. If desired, at least 2, 3, 4, 5, 6, 7, 8, 9, or 10 or more of one or more of the polypeptides may occur in the fusion protein. Multiple viral strains of HCV occur, and NS3, NS4, NS5a, and NS5b polypeptides of any of these strains can be used in a fusion protein. A representative fusion protein for use in the present invention is shown in FIG. 7, with amino acid numbering is relative to the HCV-1 polyprotein.

Alphavirus Expressing NS345 Polyprotein

Replicon Vector and Defective Helper Constructs.

A nucleic acid encoding NS345 was generated by PCR amplification of NS3-NS5, and then the cDNA (aa 1027-

3012) was inserted into the VCR-Chim2.1 (*J Virol.* 2003, 77: 10394-403) replicon vectors, resulting in constructs VEE/SIN-NS345.

Production of Alphavirus Replicon Particles.

Replicon particles expressing HCV-NS345 were harvested as culture supernatants at 24 h post electroporation, clarified by filtration, and purified by cation exchange chromatography. Replicon particle titers were determined by intracellular staining of expressed NS3, NS4, NS5a and NS5b, following overnight infection of BHK-21 cells with serial dilutions of particles. Infected cells were permeabilized and fixed by using a Cytofix/Cytoperm kit (Pharmingen) and then stained with antibodies to HCV NS3, NS4, NS5a and NS5b and Alexa fluor 488-conjugated anti-mouse IgG. Using flow cytometry analysis, the percentage of NS3, NS4, NS5a and NS5b-positive cells was determined and used to calculate titers. The absence of contaminating replication-competent virus was determined by five consecutive infections of naive BHK-21 cell and determination of titers. Finally, endotoxin levels were measured for all replicon particle samples and shown to be <0.03 endotoxin unit/ml.

Ten (10) mice per group of balb/c mice were injected im with the indicated materials at week 0, 3, and 6. For prime-boost experiment, the mice were prime at week 0 and 3, and boosted at week 6. We used 5E6 replication particle of VEE/SIN-NS345 and 50 µg of poly protein (NS345core) mixed with 5 µg of ISCOMATRIX (CSL) for injection. The mice were scarified at week 8 and the spleens were harvested to detect the CD4 and CD8 response.

Intracellular Staining (ICS)

Spleen cells (1Ex6) were stimulated with 10 µg/ml of the indicated peptides for 6 hours at 37° C. in the presence of anti-CD28 (1 µg/ml) (BD Biosciences, San Jose, Calif.) and Brefeldin A (BD Biosciences, San Jose, Calif.), and then stained with antibodies for CD8 (BD Biosciences, San Jose, Calif.). The cells were then fixed and permeabilized for IFN-γ staining (BD Biosciences, San Jose, Calif.). After staining, the cells were analyzed by flow-cytometry. The data represent IFN-γ and CD8 double positive population in CD8+ T cells. NS3, NS4, NS5a or NS5b pool: 20 mer over-lapping peptides covering NS3, NS4, NS5a or NS5b region.

NS3-1 pep: LVALGINAVAYYRGL (SEQ ID NO:6) (Simon, Cornell et al. 2003)

NS3-2 pep: TTVRLRAYMNTPGLP (SEQ ID NO:7) (Simon, Cornell et al. 2003)

NS3-3 pep: SSPPVVPQSF (SEQ ID NO:8) (Arribillaga, de Cerio et al. 2002; Arribillaga, Sarobe et al. 2005)

NS5b pep: MSYSWTGALVTPCAAE (SEQ ID NO:9) (Uno-Furuta, Matsuo et al. 2003)

SOD-C100: recombinant NS4 protein purified from yeast

SOD-NS5: recombinant NS5A/B protein purified from yeast

Intracellular Staining for Inteferon-Gamma (IFN-γ).

Figure 4:
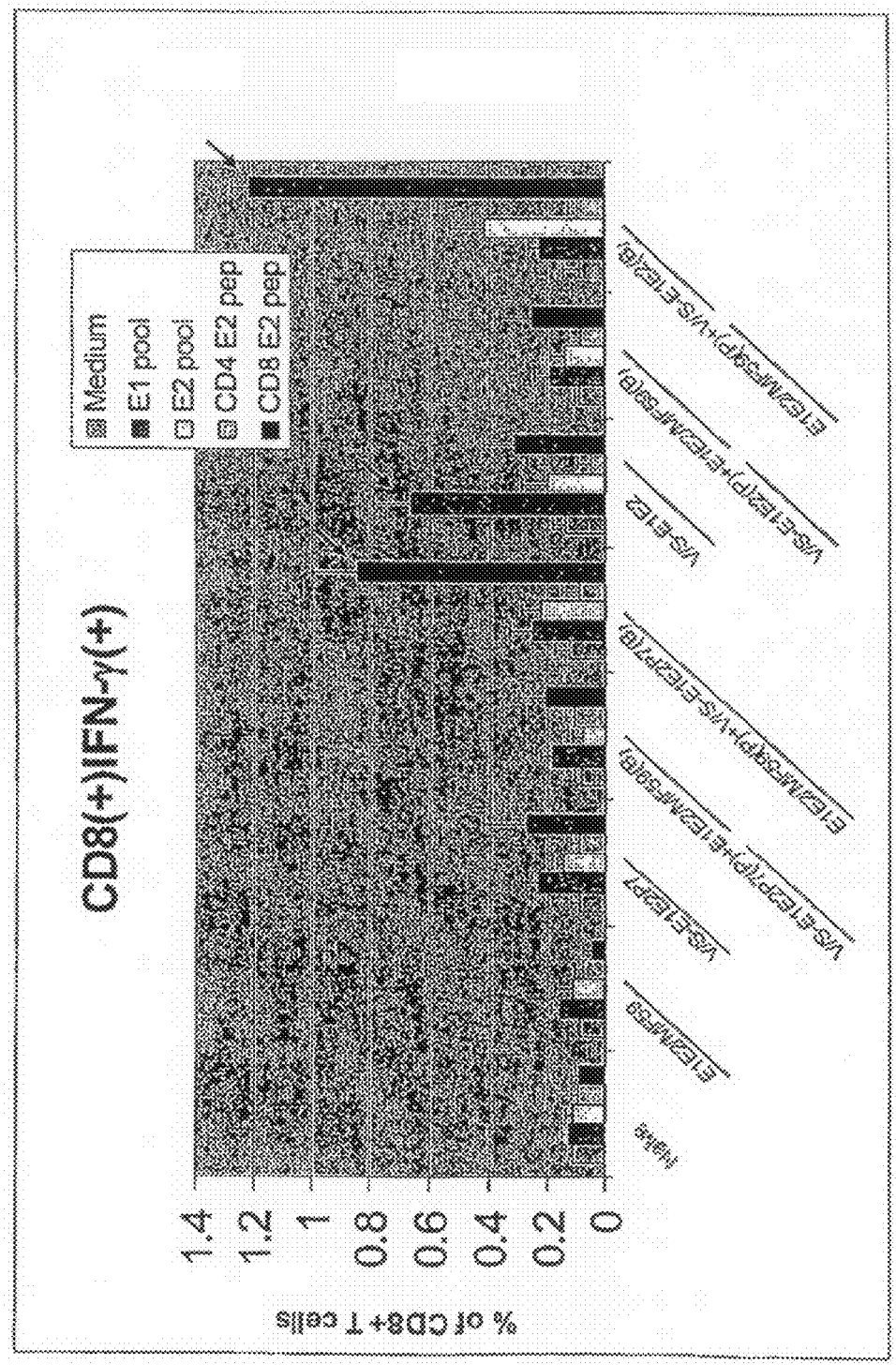
FIG. 4 shows HCV-specific CD8+ and IFN-γ expression in mice vaccinated as described in the examples.

Intracellular staining for IFN-γ was used to identify the CD8+ T cells that secrete IFN-γ after in vitro stimulation with the E1 or E2 pooled peptides, or individual CD4 E2 or CD8 E2 peptides, indicated below. In particular, 1×10⁶ spleen cells were stimulated with 10 µg/ml of the E1 or E2 peptides as indicated in FIG. 4, for 6 hours at 37° C. in the presence of anti-CD28 (1 µg/ml) (BD Biosciences, San Jose, Calif.) and Brefeldin A (BD Biosciences, San Jose, Calif.), and then stained with antibodies for CD8 (BD Biosciences, San Jose, Calif.). The cells were then fixed and permeabilized for IFN-γ staining BD Biosciences, San Jose, Calif.). After staining, the cells were analyzed by flow-cytometry.

The data represent IFN-γ and CD8 double positive population in CD8+ T cells.

E1 pool: 20mer over-lapping peptides covering the E1 region.

E2 pool: 20mer over-lapping peptides the covering E2 region.

CD4 E2 pep: QTHTTGGQAGHQAHSLTGLFSPGAKQN (SEQ ID NO: 4)

(Zucchelli et al., *J. Virol.* (2000) 74:11598-11607).

CD8 E2 pep: DATYSRCGSGPWITPRCLVD (SEQ ID NO: 5)

(Zucchelli et al., *J. Virol.* (2000) 74:11598-11607).

Epitopes of NS proteins and fusion proteins described herein can be identified by several methods. For example, NS3, NS4, NS5a, NS5b polypeptides or fusion proteins comprising any combination of the above, can be isolated, for example, by immunoaffinity purification using a monoclonal antibody for the polypeptide or protein. The isolated protein sequence can then be screened by preparing a series of 20 short peptides by proteolytic cleavage of the purified protein, which together span the entire protein sequence. By starting with, for example, 100-mer polypeptides, each polypeptide can be tested for the presence of epitopes recognized by a T-cell receptor on an HCV-activated T cell, progressively smaller and overlapping fragments can then be tested from an identified 100-mer to map the epitope of interest.

Example 1

Immunization of Mice Using E1E2 or E1E2P7 Replicons

Balb/c mice were immunized three times with PBS (naïve), VEE/SIN chimeric alpha virus replicons (4E+6 or 4E+5 replication particle of V/S-E1E2 and V/S-E1E2P7), E1E2P7 protein plus MF59, and E1E2P7 protein plus MF59 and CpG. The mice were immunized at week 0 and 3, and 6, and then the spleens were harvested at week 8. The spleen cells were stimulated with 10 ug/ml of HCV peptide pools (E1 pool and E2 pool) or individual peptides (CD4 E2 pep and CD8 E2 pep) and then stained with antibody for CD8 and IFN-γ for flow cytometry analysis. The data present the percentage of the IFN-γ positive population in the CD8+ T cells after the immunization. As the red arrow indicated, prime with V/S-E1E2 or V/S-E1E2P7 could stimulate very good CD8+ T cells response for IFN-γ production.

Figure 3:
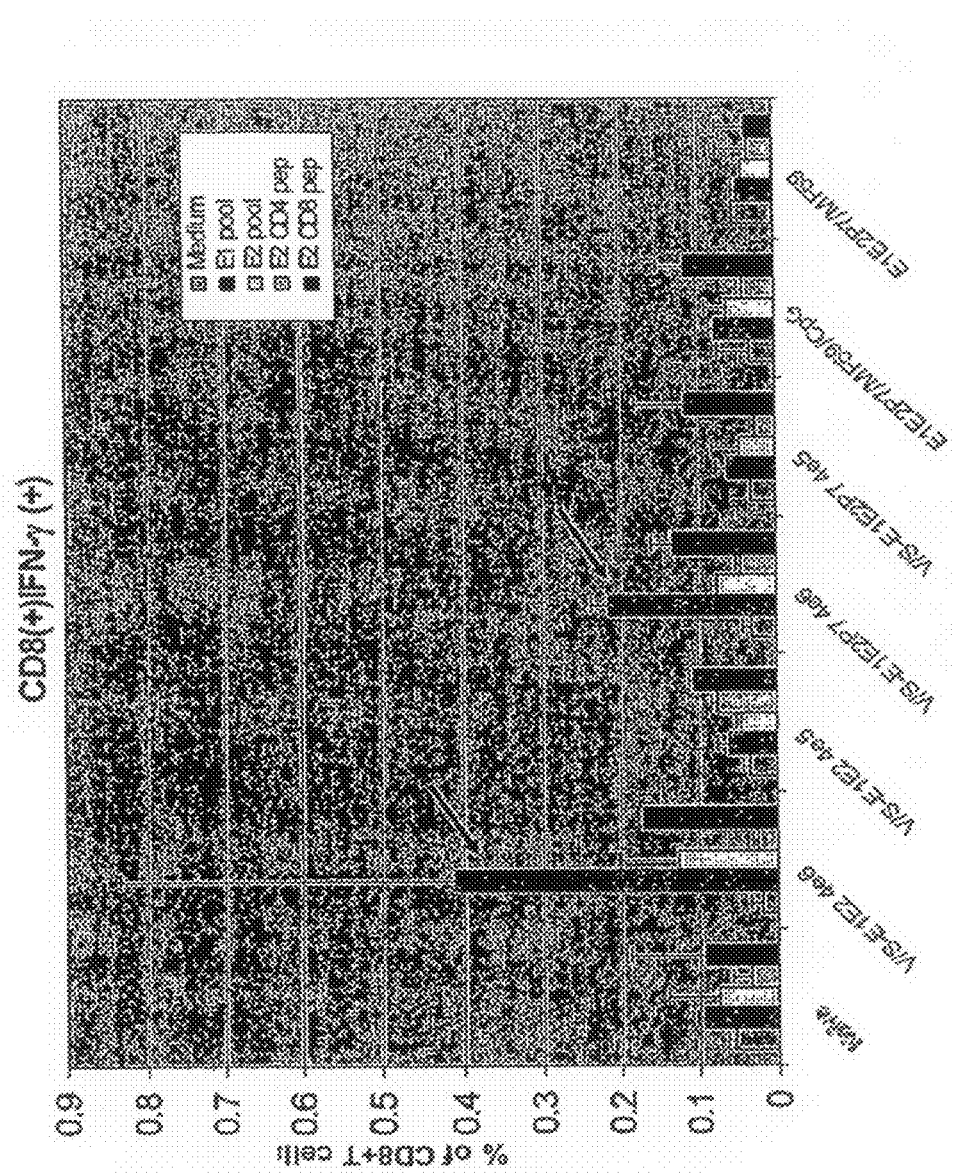
FIG. 3 shows HCV-specific CD8+ and IFN-γ expression in mice vaccinated as described in the legend and examples.

Results are shown in FIG. 3. As can be seen, VEE/SIN-E1E2 and VEE/SIN-E 1E2P7 replicons both stimulated a robust CD8+ T cells response to the E1 protein, but did not stimulate an HCV specific CD4+ T cell response (FIG. 5*a*). These results demonstrate that when a polynucleotide encoding E1E2 antigen without P7 is delivered with a defective alpahvirus particle without being preceded by an E1E2P7/MF59 protein prime, the CD8+ T cell response to E1 antigen is enhanced.

Example 2

Immunization of Mice Using E1E2P7 Protein Vaccines Followed by E1E2 or E1E2P7 Chimeric Replicons Particle Boosts The following studies were conducted to determine the effect of E1E2P7 primary immunizations followed by E1E2 replicon boosts on HCV-specific T cell responses. Balb/c mice (10 mice per group) were injected intramuscularly (im) with the indicated materials (FIG. 4) at week 0, 3, and 6, and the serum was collected at week 2, 5, and 8. For the prime-boost experiment, the mice were primed at week 0 and 3 with E1E2P7 protein plus MF59, and boosted with the indicated chimeric replicon particles at week 6. $4 \times 10^6$ replication particles of VEE/SIN-E1E2 and VEE/SIN-E1E2$_{809}$ (also termed E1E2P7) were used and 2 μg of E1E2 protein complexes (E1E2$_{809}$ derived from expression of the E1E2$_{809}$ construct described above in Materials and Methods, "*Production of E1E2$_{809}$ protein*") was emulsified with MF59 for injection. E1E2/MF59 protein production is described for example in WO03/002065 The mice were sacrificed at week 8 and the spleens were harvested to detect the CD4 and CD8 response.

Results are shown in FIG. 4. As can be seen, VEE/SIN-E1E2 stimulated a robust CD8$^+$ T cells response, but did not stimulate an HCV specific CD4$^+$ T cell response (FIG. 5a). As indicated in FIG. 4, priming with E1E2$_{809}$/MF59 followed by boosts with "VEE/SIN-E1E2" or "VEE/SIN-E1E2$_{809}$" (also referred to as E1/E2 P7) stimulated very good CD8 T cell responses for IFN-γ production. The ultimate priming of CD8$^+$ T cell responses was attained by first priming with E1E2$_{809}$/MF59 followed by boosting with VEE/SIN-E1E2. These results evidence that the above-described prime-boost regimen may be beneficial in prophylactic and therapeutic vaccine approaches against HCV, since this regimen results in an increase in an HCV E2-specific CD8+ response.

Example 3

Immunization of Mice Using E1E2P7 Plus CpG Protein Vaccines Followed by E1E2 or E1E2P7 Chimeric Replicons Particle Boosts Immunizations as in Example 2 were performed but in this Example CpG was added to the E1/E2 protein prime immunogenic compositions. All methods were as above and E1/E2 protein was diluted to 2 ug in 50 ul. This 50 ul of protein was added to 50 ul MF59, to which 1 ul of CpG (concentration 10 ug/ul) was added. Following protein priming as above, chimeric alphavirus encoding E1/E2 (i.e., VEE/SIN-E1E2) was used for boosting immunizations.

Figure 5B:
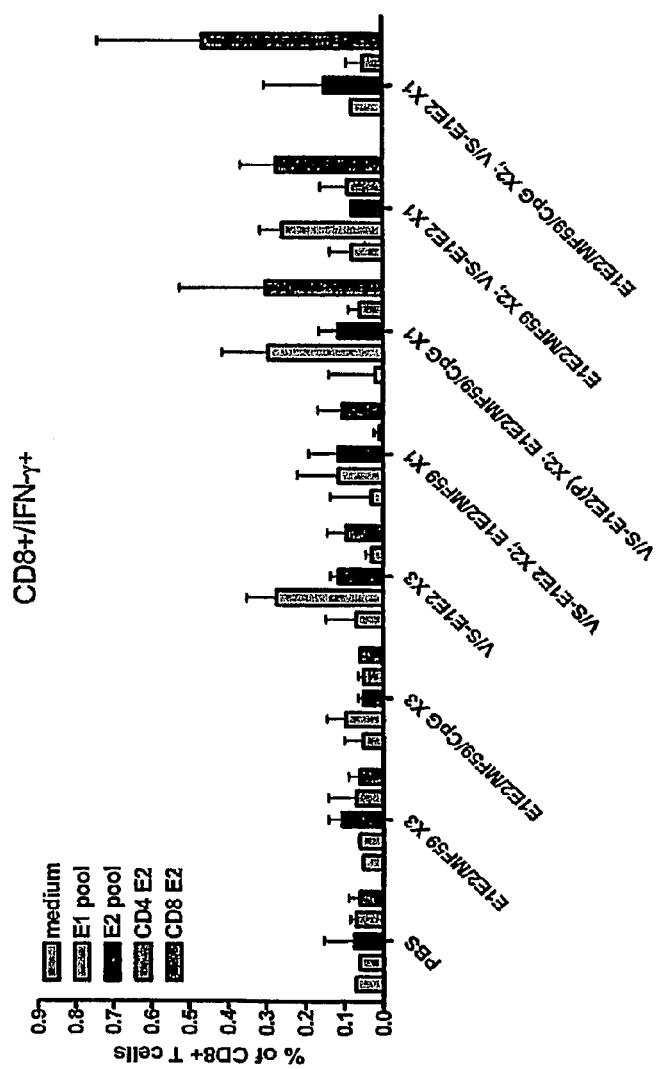
FIG. 5b shows HCV-specific CD8+ and IFN-γ expression in mice vaccinated as described in the examples.

Results of adding CpG to the E1/E2 MF59 priming regimen are shown in FIGS. 5a and 5b.

Figure 6:
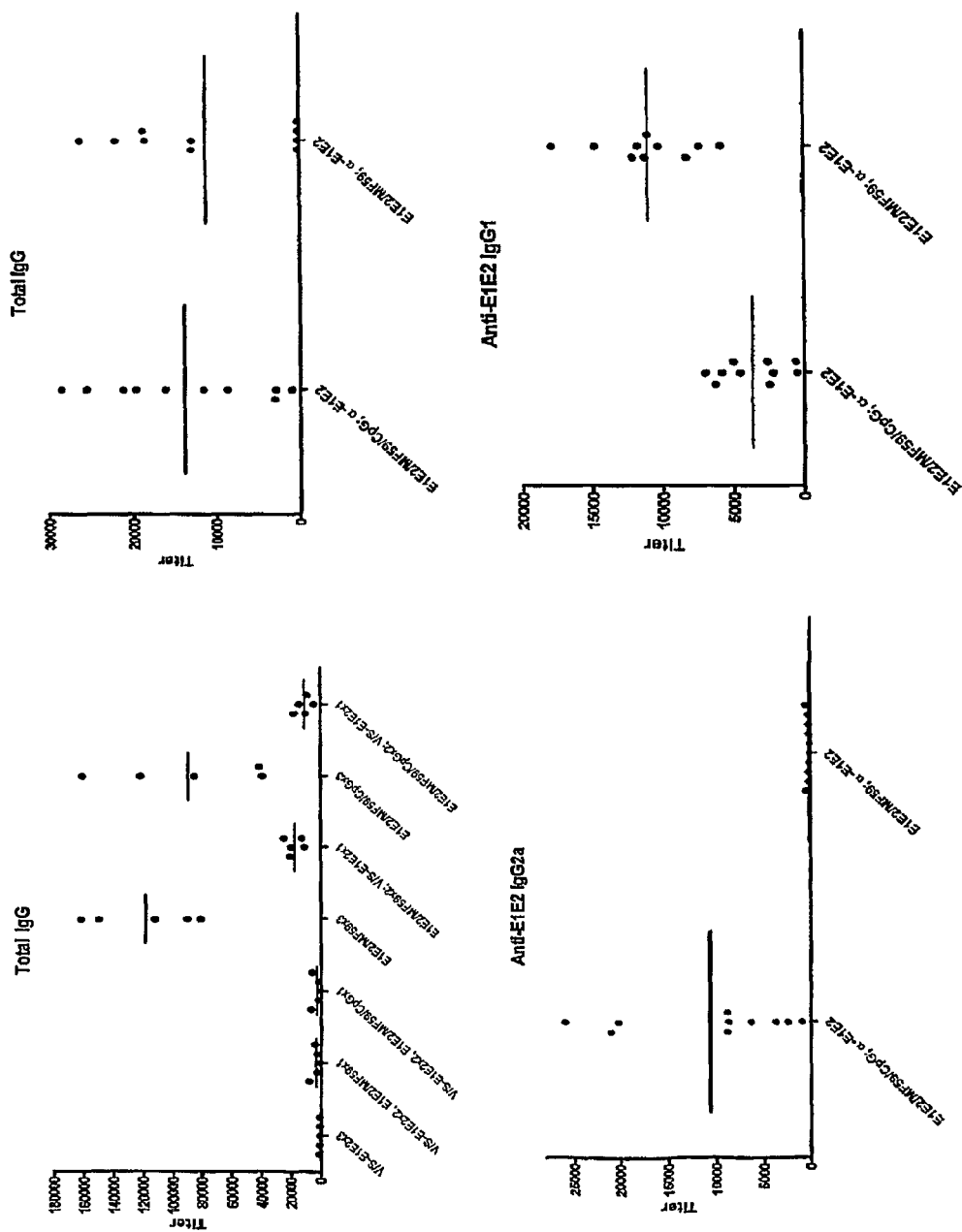
FIG. 6 shows the results of ELISA assays for determination of antibody production as described in the examples.

Determination of IgG isotype response following various immunization strategies were performed. Results are shown in FIG. 6. Referring now to FIG. 6, it is shown that E1E2/MF59 and E1E2/MF59/CpG immunization induced equivalent Ab response, but different IgG1/2a ratios. Also, prime/boost regimen without CpG induced an antibody Ab response which was higher than alphavirus encoding E1/E2 alone, but lower than protein alone.

The CpG sequence "7909" was used in these experiments was in 5' to 3' direction TCGTCGTTTTGTCGTTTTGTCGTT (SEQ ID NO:10). (See, e.g. U.S. Pat. No. 6,239,116.) CpG 7909 is a 24-mer B-Class CpG oligodeoxynucleotide (*Vaccine*, 2004 Aug. 13; 22(23-24):3136-43.)

Example 5

Antibody titers to E1 and E2 were also examined following prime boost with an E1/E2 regimen. Alphavirus alone encoding E1/E2 or E1/E2P7 did not elicit significant anti E1 or E2 responses but when administered as part of a prime with E1/E2 protein and boosting with alphavirus encoding E1/E2, antibody to E1 and E2 were produced. Isotype response to prime-boost regimens for E1/E2 were compared between protein prime with and without CpG as part of the protein priming step. As shown in FIG. 6, when CpG was administered with protein priming, the immune response resembled a TH1 response (increased IgG2A) while without CpG a TH2-like response (increased IgG1) was induced.

Example 6

Neutralization of Binding Antibodies

Antibody Titers for Blocking E1E2 to CD81

A quantitative cytofluorimetric assay was used to assess the binding of hepatitis C envelope glycoprotein to human cells (Proc. Natl. Acad. Sci. USA Vol. 93, pp. 1759-1763, 1996; Science Vol. 282, pp. 938-941, 1998). This assay has demonstrated a positive correlation between chimpanzee protective antibody titer and the ability of these antibodies to inhibit recombinant E2 protein from binding to target cell. Human CD81, a member of the tetraspanin super family, binds recombinant E2 protein and, most important, the envelope associated HCV RNA. The binding site of HCV E2 was mapped to major extra cellular loop of CD81 (EC2) that is conserved in both humans and chimpanzees. A recombinant fusion molecule containing the large extra cellular loop of human CD81 fused to the C-terminal end of the thioredoxin was cloned, expressed and purified. Our assay data suggests HCV protective antibodies derived from chimpanzees immunized with an E1/E2 vaccine can inhibit both E1/E2 and E2 protein binding to CD81. CD81 recombinant receptor protein is coated onto 96-well plates. Anti-E2 specific monoclonal antibody with Europium labeled is Used for detection.

CD81 recombinant receptor, 250 ng per assay, in Sodium Borate buffer was coated in 96 well medium binding Costar plate (Plate A) overnight. Dilute separately antigen CHO E1/E2 (5 ug/ml) and Moab 5E5/H7*Eu3+(0.33 ug/ml in working reagent. In a dilution plate (Plate B), 55 ul diluted CHO E1/E2 was added together with 55 ul 5E5/H7-Eu3+ Moab in working reagent to each, well. The plates were shaken for 15 minutes at 40° C. Then to each well of plate B an additional 110 ul diluted sera sample two-fold dilution in PBS/BSA buffer was added, shaken for 45 min. at 40° C. 200 ul of the content from each well of plate B was transferred to the CD81 coated plate (Plate A) accordingly. The plate was shaken for 45 min. at 40° C. The plate was washed five times with wash buffer (1×PBS, 0.1% Tween-20) and 200 ul per well Enhancement Solution (Wallac) was added to each well and shaken for 5 min. at room temperature. The plate was placed in Wallac 1420 Multilabel Counter and read with protocol 'Europium'.

50% inhibition multiplied by the dilution factor was used to estimate the CD81 titer. The pre-immunized bleed of a given subject at the assay dilution 1:10 was used as the negative control. Percent inhibition was estimated for each post-immunized bleed date by using the following formula:

% Inhibition is equal to: (Signal of Negative Control–Signal of Sample)/Signal of Negative Control× 100%.

Figure 12:
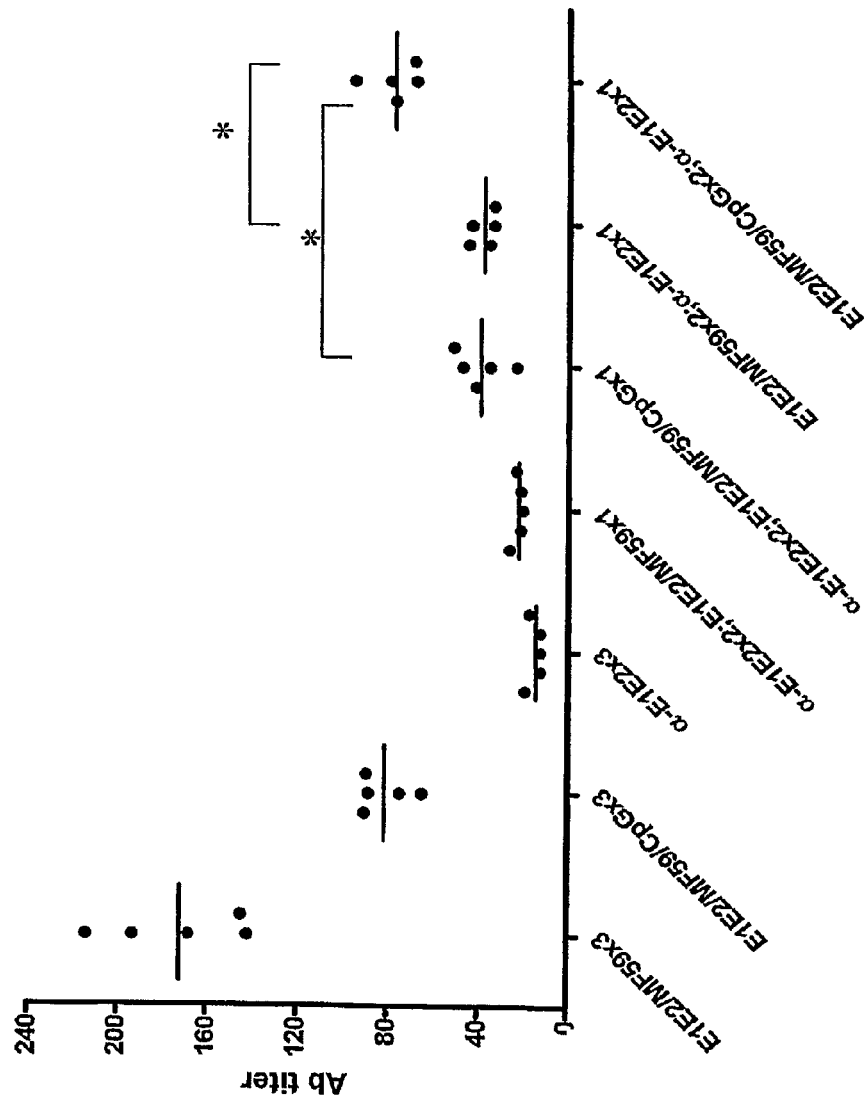
FIG. 12 shows graphically the results of neutralizing antibody titers (i.e., antibody titers for blocking E1E2 binding to CD81) generated in mice immunized with a prime boost regimen of E1E2 as described in the examples.

Results of Neutralizing antibody (i.e., antibody titers for blocking E1E2 to CD81) generated with various vaccine regiments described herein are provided in FIG. 12. These results demonstrate that E1E2 polyprotein plus MF59 and optionally CpG produced the highest neutralizing antibody titers but that immunization with a regimen of priming with E1/E2 MF59 plus CpG followed by boosting with defective alphavirus encoding E1E2 also produced significant neutralizing of binding antibodies. E1E2 glycoprotein plus MF59 and without CpG produced the highest neutralizing (i.e., anti-CD81) antibody titers but immunization with a regimen of priming with E1/E2 MF59 plus CpG followed by boosting with defective alphavirus encoding E1E2 and immunizing with E1E2 glycoprotein plus MF59 and CpG also produced significant neutralizing of binding antibodies (anti-CD81).

Example 7

Immunization of Mice Using E2NS345core121 Protein Plus ISCOMS

Balb/c mice were immunized three times with PBS (naïve), VEE/SIN chimeric alpha virus replicons encoding Green Fluorescent Protein or NS345 (5E+5 or 5E+6). The mice were immunized at week 0 and 3, and 6, and then the spleens were harvested at week 8. The spleen cells were stimulated with 10 ug/ml of HCV peptide pools and then stained with antibody for CD4 (FIG. 8) or CD8 FIG. 9), and IFN-γ for flow cytometry analysis. The data present the percentage of the IFN-γ positive population in the CD8+ or CD4+ T cells after the immunization.

Results are shown in FIGS. 8 and 9. As can be seen, VEE/SIN-NS345 replicons Induced broad HCV-specific CD4+ and CD8+ T cell responses especially CD8+ T cell responses.

Example 8

Immunization of Mice Using NS345core/ISCOM Protein Vaccine Prime Followed by Alphavirus Chimeric Replicons Encoding NS345 Protein Regions as Described Above for Particle boosts A synthetic HCV1a nucleic acid encoding an HCV fusion protein consisting of, in an amino to carboxy sequence the sequence of amino acids 384-715 of E2, amino acids 1018 to 1026 of NS2, amino acids 1027 to 1657 of NS3, amino acids 1658 to 1972 of NS4, amino acids 1973 to 2990 of NS5 and amino acids 1 to 121 of core, wherein the serine at position 1165 of the NS3 sequence is replaced with an alanine, amino acid 9 of the core sequence is a lysine and amino acid 11 of the core sequence is arginine. was constructed. This sequence is represented schematically in FIG. 7 with amino acid numberings relative to the HCV-1 sequence.

In one embodiment, the invention comprises HCV NS polyproteins having a mutation in NS3 which inactivates the protease activity. Such mutations enable expression of a fusion protein, as described in WO2004/005473. Additionally, in one embodiment, the invention comprises HCV NS polyproteins further comprising one or more structural protein sequences from HCV in the fusion protein is also preferred.

The fusion protein encoded therein was expressed in yeast *Sacchromyces cerevisiae*. The fusion protein was cloned and expressed from plasmid pBS24.1 further containing the fusion protein insert DNA utilizing standard recombinant cloning techniques and in particular those methods described previously in US2006-0088819A1, WO01/38360 and WO2004/005473. The above fusion protein is designated "e2 ns$3_m$ns5tr.c121" or "E2NS3*NS4NS5tcore121"

The e2ns$3_m$ns5tr.c121polyprotein was genetically engineered for expression in *Saccharomyces cerevisiae* using the yeast expression vector pBS24.1 (U.S. Pat. No. 6,458,527 section 4.2.4.2 and U.S. Pat. No. 5,635,374). This vector contains the 2μ sequence for autonomous replication in yeast and the yeast genes leu2d and URA3 as selectable markers. The α-factor terminator, β-lactamase gene and the ColE1 origin of replication, required for plasmid replication in bacteria, are also present in this expression vector.

The following steps were taken to construct the expression cassette for the e2ns$3_m$ns5tr.c121 polyprotein:

First, to assemble the N-terminus region, a HindIII/AclI fragment of 819 bp was gel isolated from pGEM7.d.E2 (HindIII/XhoI) subclone #3. The 5' HindIII cloning site is followed by the sequence ACAAAACAAA, the inititator ATG, and codons for the HCV-1 E2 ectodomain, beginning at aa384 and continuing to an AclI restriction site at aa650. The HindIII/AclI fragment and a 34 bp AclI/CelII kinased synthetic fragment, corresponding to aa651-aa662 of the E2 ectodomain, were ligated into a pT7Blue2 HindIII/CelII vector containing a 228 bp CelII/BlnI fragment which encodes aa662 to aa715 of the HCV-1 E2 ectodomain sequence, followed by codons for aa1018-aa1039 of HCV-1 NS2 and NS3. The ligation mixture was transformed into HB101 competent cells and plated onto Luria-ampicillin agar plates (100 μg/ml). After miniprep DNA analysis, identification of the desired clones and sequence confirmation, pT7Blue2.E2/ns2.3 #23 was digested with HindIII and BlnI to isolate a 1081 bp fragment.

Secondly, to introduce the $Ser_{1165}$-Ala mutation in the NS3 domain, a BlnI/ClaI fragment of 703 bp was gel isolated from pSP72 HindIII/ClaI.ns3mut 1165 #15. This 703 bp fragment encodes aa1040-aa1274 of the HCV-1 genome in which $Ser_{1165}$ was mutated to Ala by site-directed mutagenesis.

Third, to facilitate the cloning of the e2.ns$3_m$-ns5core121 expression cassette, the 1081 bp HindIII/BlnI fragment and the 703 bp Bln/ClaI fragment were ligated into the pSP72 HindIII/ClaI vector. The ligation mixture was transformed as above, and after DNA analysis the resultant clone was named pSP72.HindIII/Cla e2.ns$3_m$#1

Fourth, a 1784 bp HindIII/ClaI fragment was gel purified from pSP72.HindIII/Cla e2.ns$3_m$#1 described above. A ClaI/NheI 2787 bp fragment encoding aa1274-aa2202 from NS3-NS5a of HCV-1 was isolated from a full-length HCV-1 clone, pUC.HCV3. A 2732 bp Nhe/SalI fragment was gel isolated from a pSP72.HindIII/SalI.ns5ab.2990.core121 #27 subclone. The Nhe/Sal fragment corresponds to aa2203-2990 of NS5a and NS5b, followed by aa1-121 of the core domain. Within the HCV-1 core sequence, consensus aa were incorporated at position 9 (Lys) and 11 (Arg).

Lastly, the 1366 bp BamHI/HindIII ADH2/GAPDH promoter fragment, described in the U.S. Pat. No. 6,183,985, was ligated with the 1784 bp HindIII/ClaI fragment, the 2787 bp Cla/NheI fragment, and the 2732 bp NheI/SalI fragment into the pBS24.1 BamHI/SalI yeast expression vector, thereby creating plasmid pd.e2 ns$3_m$ns5tr.c121.

*S. cerevisiae* strain AD3* genotype (matα,leu2,trp1,ura3-52,prb-1122,pep4-3,prc1-407, cir$^o$,trp+, :DM15[GAP/ADR], was transformed with pd.e2ns$3_m$ns5tr.c121 yeast expression plasmid, yeast cells were transformed with the expression plasmid using a lithium acetate protocol. Ura-transformants were streaked for single colonies and patched onto leu-/8% glucose plates to increase plasmid copy number. Leu-starter cultures were grown for 24 hours at 30° C. and then diluted 1:20 in YEPD (yeast extract bactopeptone 2% glucose) media. Cells were grown for 48 hours at 30° C. and harvested after depletion of glucose in the medium. To test for expression of the e2ns$3_m$ns5tr.c121 recombinant antigen, aliquots of cells were lysed with glass beads in lysis buffer (10 mM Tris-Cl pH 7.5, 1 mM EDTA, 10 mM DTT). The lysates were cleared by centrifugation at high speed. Aliquots of the soluble and insoluble fractions were boiled in SDS sample buffer pH12+50 mM DTT, run on 4-20% Tris-Glycine gels, and stained with Coomassie blue. The recombinant protein was detected in the insoluble fraction after glass bead lysis.

*S. cerevisiae* strain AD3* is derived originally from strain BJ2168 described in U.S. Pat. No. 6,458,527 section 4.2.4.42"

The E2NS3*NS4NS5tcore121 fusion protein was expressed from a yeast plasmid using the ADH2/GAPDH promoter. The E2NS345tcore121 fusion protein comprises from the amino to carboxy terminus amino acids 384-715 (E2)-1018-1026 (NS2)-1027-1972(NS3NS4)-1973-2990 (NS5t)-1-121 (Core). The amino acid numbering is relative to the full length HCV polyprotein and the NS3 and core are modified as indicated above.

The E2NS3*NS4NS5tcore121 protein produced as described above was used to produce HCV fusion-ISCOMs as follows. The fusion-ISCOM formulations were prepared by mixing the fusion protein with a preformed ISCOMATRIX (empty ISCOMs) utilizing ionic interactions to maximize association between the fusion protein and the adjuvant. ISCOMATRIX is prepared essentially as described in Coulter et al. (1998) *Vaccine* 16:1243. Further methods for production of HCV polyproteins plus ISCOMs The fusion-ISCOM formulations are also referred to herein as "IMX/poly".

Figure 10:
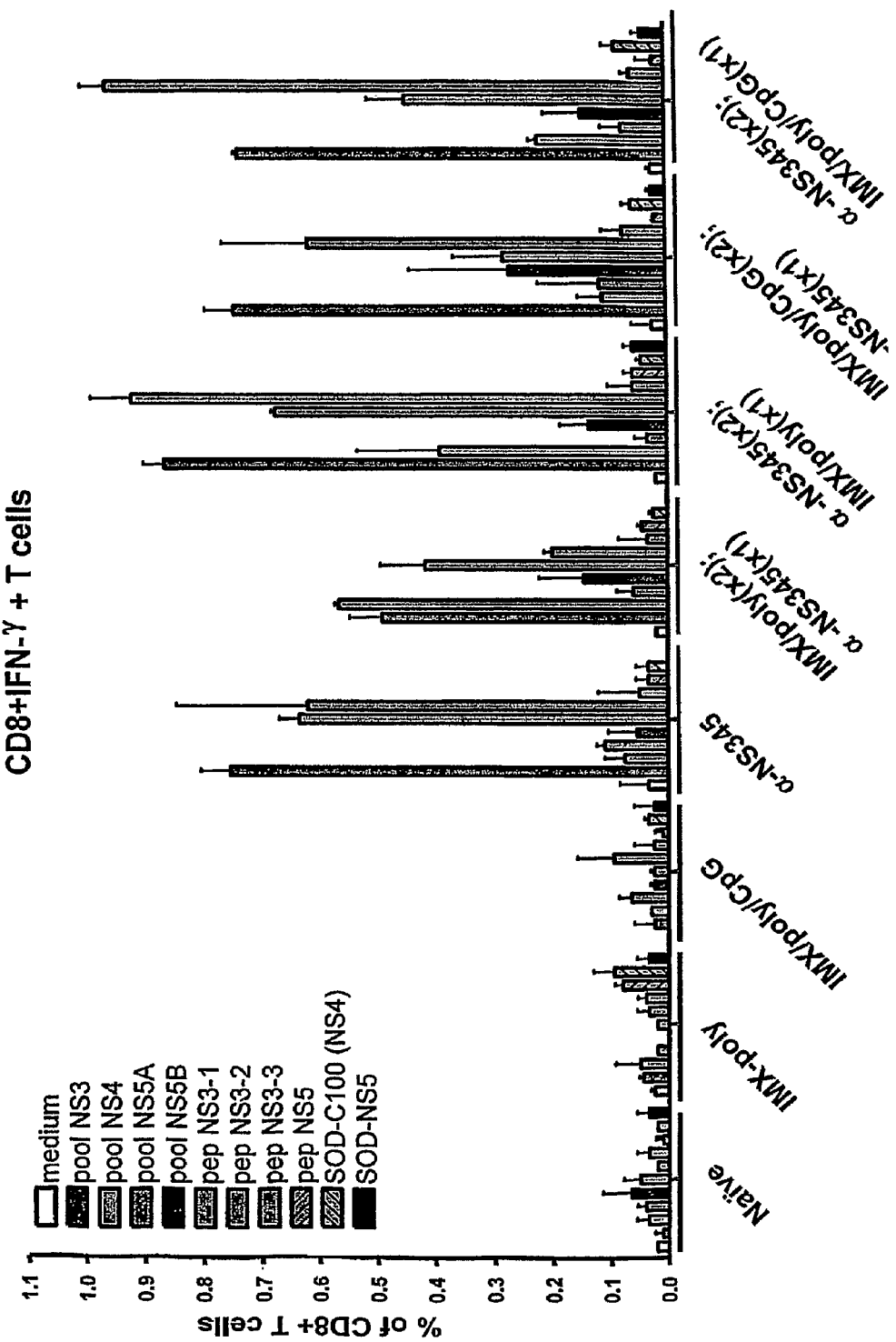
FIG. 10 shows graphically the results of CD8 HCV specific T cells generated following immunization with various NS alphavirus and or NS polypeptide constructs as described in the examples.
Figure 11:
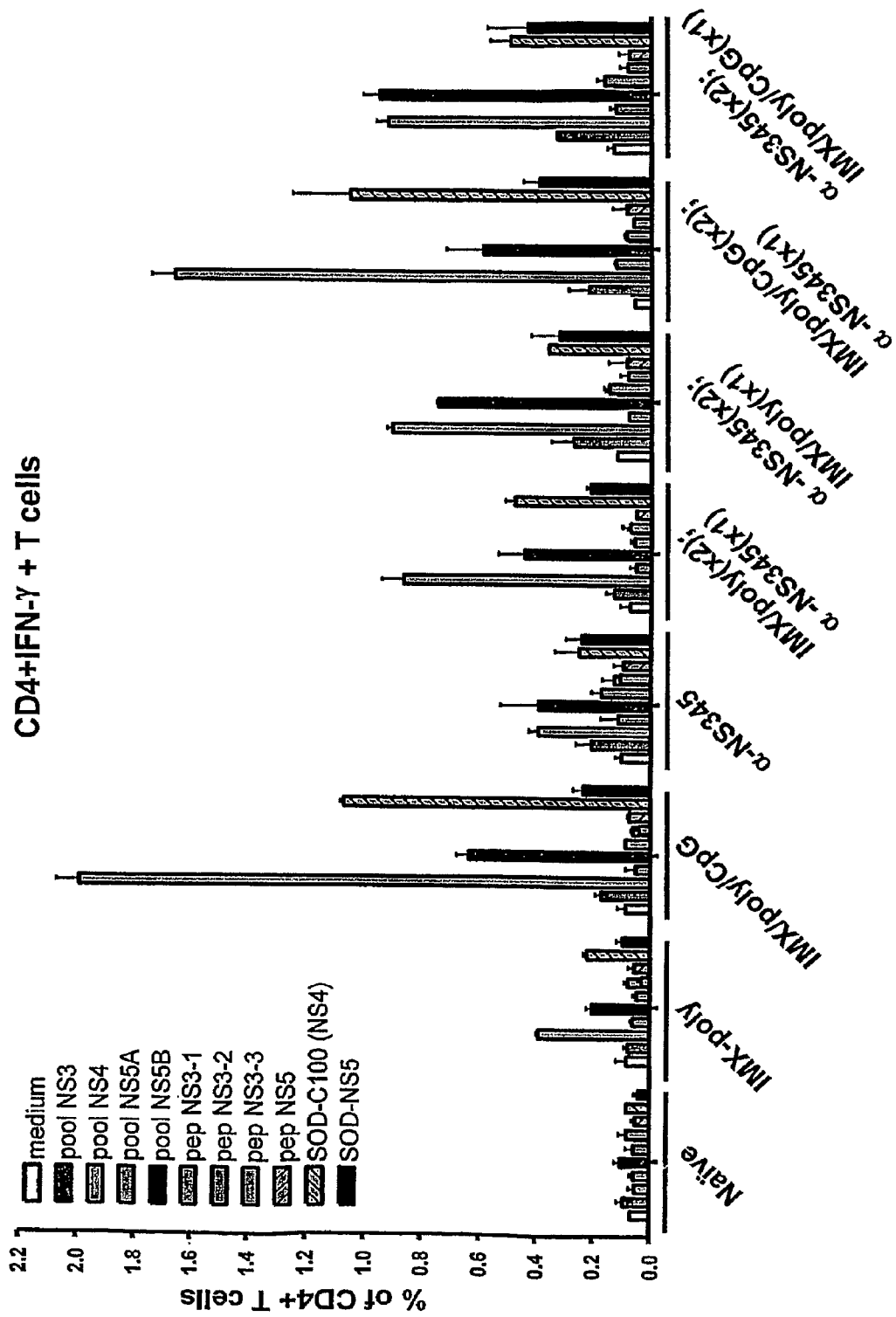
FIG. 11 shows graphically the results of CD4 HCV specific T cells generated following immunization with various NS alphavirus and or NS polypeptide as described in the examples.

The following studies were conducted to determine the effect of E2NS3*NS4NS5tcore121/ISCOMS with or without CpG primary immunizations followed by NS345 replicon boosts on HCV-specific T cell responses. Alternatively, immunizations were reversed and the alphavirus encoding NS345 was administered before the fusion-ISCOM formulations. Balb/c mice (10 mice per group) were injected intramuscularly (im) with the indicated materials (FIGS. 10 and 11) at week 0, 3, and 6, and the serum was collected at week 2, 5, and 8.

Example 9

Cross Neutralizing Abs that Blocks JFH1-HCVcc (HCV-2a) Infection to Huh7 Cells

The immune sera from various prime boost regimens as described herein were analyzed for ability to neutralize infectivity of a heterologous HCV strain in an HCV tissue culture assay. An HCV genomic construct encoding the type 2a HCV strain with a Luciferase reporter gene provided in a monocistronic configuration with the JH1 genome was generated and called as JFH1 2a HCVcc. In this assay, replication of the JFH1 luciferase is detected by observing the luciferase activity as Relative light units (RLU), which in turn is represented as % of control (injection with PBS) in FIG. 13. The JFH-1 Luciferase construct packaged in infectious particles was used to infect hepatocytes. Infection was allowed to occur after viral particles were treated for 1 hour at 37° C. and then used to infect HuH7 cells. The infected cells were incubated for three days and then assayed for luciferase activity.

Figure 13:
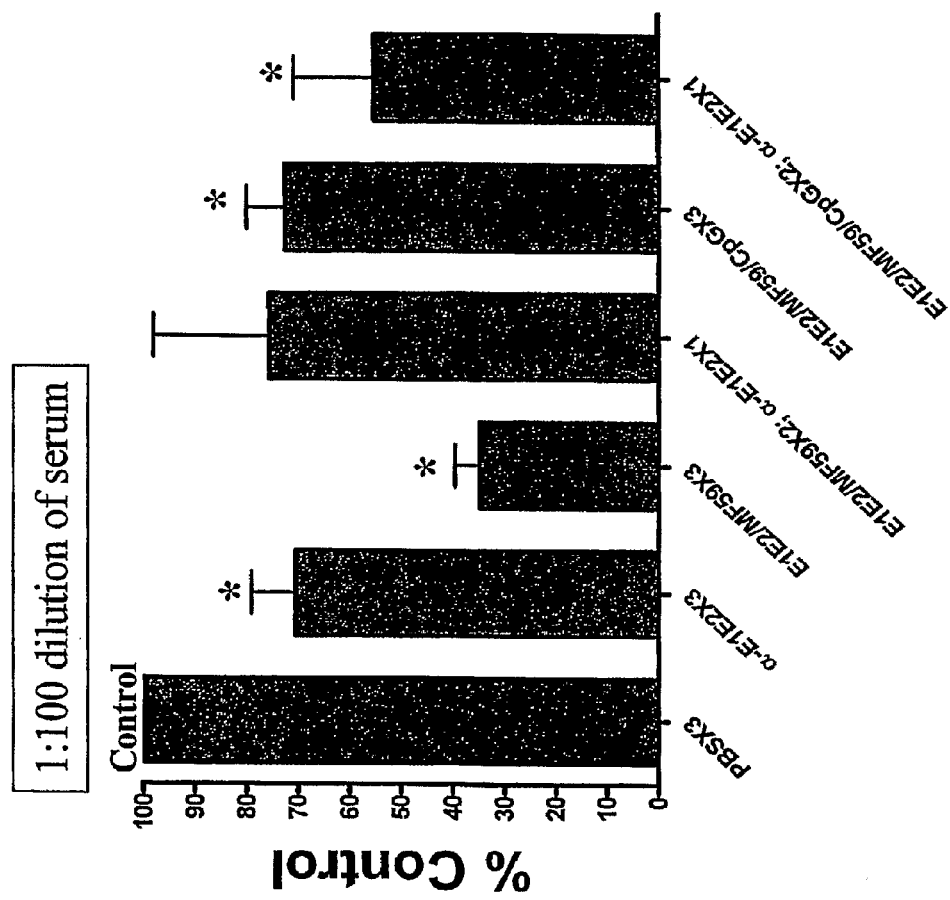
FIG. 13 shows graphically the results of prevention of infectivity by prime boost sera in an HCV cell culture/luciferase assay (i.e., an HCVcc neutralizing assay).

The results of this Example with mice demonstrate that prime boosting with E1/E2 MF59/CpG followed by alphavirus encoding E1E2 from HCV1a generated neutralizing antibodies that neutralized infection of a heterologous 2a HCV type, JFH1 2a HCVcc (FIG. 13). Previous Examples demonstrated that this particular prime boost combination also elicits a significant T-cell response.

Figure 14:
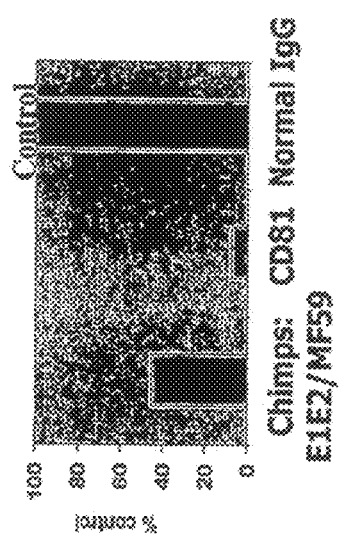
FIG. 14 demonstrates graphically the prevention of infectivity for an HCV cell culture/luciferase assay, in particular the HCVcc neutralizing assay.

FIG. 14 demonstrates that immune sera from a chimp that was immunized with E1E2 MF59 and purified CD81 protein cause a reduction in luciferase activity under the conditions used for mice sera in this example. This control demonstrates the utility of the assay for detecting neutralization.

Although preferred embodiments of the subject invention have been described in some detail, it is understood that obvious variations can be made without departing from the spirit and the scope of the invention as defined by the claims.

The invention claimed is:

1. A method of activating T cells of a vertebrate subject, wherein said T cells recognize an epitope of a hepatitis C virus (HCV) polypeptide, said method comprising:
   administering at least once a first composition comprising an HCV E1E2 protein complex to said vertebrate subject; and
   subsequently administering at least once a second composition comprising a viral vector comprising a nucleic acid sequence encoding a HCV E1 and HCVE2 polypeptide to said vertebrate subject, whereby an HCV E1E2 complex is expressed in one or more cells of the subject, wherein the viral vector is a chimeric defective alphavirus particle;
   whereby T cells are activated in said subject and said activated T cells recognize an epitope of E1 and/or E2 polypeptide.

2. The method of claim 1, wherein the subject is infected with HCV prior to administration of one or more of said first and second compositions.

3. The method of claim 1, wherein the subject is not infected with HCV prior to administration of one or more of said first and second compositions.

4. The method of claim 1, wherein the T cells comprise CD8+ T cells.

5. The method of claim 4, wherein the CD8+ T cells express interferon-γ.

6. The method of claim 1, wherein the first composition comprising an HCV E1E2 complex further comprises an adjuvant.

7. The method of claim 6, wherein the adjuvant is a submicron oil-in-water emulsion.

8. The method of claim 7, wherein the submicron oil-in-water emulsion comprises 4-5% w/v squalene, 0.25-1.0% w/v polyoxyelthylenesorbitan monooleate, and/or 0.25-1.0% sorbitan trioleate, and optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE)).

9. The method of claim 8, wherein the submicron oil-in-water emulsion is MF59.

10. The method of claim 1, wherein the E1E2 complex in the protein composition is produced by expression of a polynucleotide encoding a sequence of amino acids having at least 80% sequence identity to the sequence of amino acids depicted at positions 20-637 of SEQ ID NO:2.

11. The method of claim 10, wherein the HCV E1E2 complex in the protein composition is produced by expression of a polynucleotide encoding the sequence of amino acids depicted at positions 20-637 of SEQ ID NO:2.

12. The method of claim 1, wherein the viral vector comprising a nucleic acid sequence encoding a HCV E1 and E2 polypeptide having at least 80% sequence identity to the sequence of amino acids depicted at positions 20-574 of SEQ ID NO:2.

13. The method of claim 12, wherein the viral vector comprising a nucleic acid sequence encoding a HCV E1 and E2 polypeptide depicted at positions 20-574 of SEQ ID NO:2.

14. The method of claim 1, wherein the viral vector comprising a nucleic acid sequence encoding a HCV E1 and E2 polypeptide having at least 80% sequence identity to the sequence of amino acids depicted at positions 20-637 of SEQ ID NO:2.

15. The method of claim 14, wherein the viral vector comprising a nucleic acid sequence encoding a HCV E1 and E2 polypeptide depicted at positions 20-637 of SEQ ID NO:2.

16. The method of claim 1, wherein the first composition further comprises a CpG oligonucleotide.

17. The method of claim 16 wherein the CpG oligonucleotide comprises in a

5'-3' direction
5TCGTCGTTTTGTCGTTTTGTCGTT-3.           (SEQ ID NO: 10)

18. The method of claim 1, wherein the chimeric defective alphavirus replicon particle is derived from Venezuelan Equine Encephalitis virus (VEE), and Sindbis virus (SIN).

* * * * *

SEQUENCE LISTING

```
<160> NUMBER OF SEQ ID NOS: 10

<210> SEQ ID NO 1
<211> LENGTH: 1914
<212> TYPE: DNA
<213> ORGANISM: Hepatitis C virus-1

<400> SEQUENCE: 1
tctttctcta tcttccttct ggccctgctc tcttgcttga ctgtgcccgc ttcggcctac      60
caagtgcgca actccacggg gctctaccac gtcaccaatg attgccctaa ctcgagtatt     120
gtgtacgagg cggccgatgc catcctgcac actccggggt gcgtcccttg cgttcgcgag     180
ggcaacgcct cgaggtgttg ggtggcgatg accccctacgg tggccaccag ggatggcaaa     240
ctccccgcga cgcagcttcg acgtcacatc gatctgcttg tcgggagcgc caccctctgt     300
tcggccctct acgtggggga cctgtgcggg tctgtctttc ttgtcggcca actgtttacc     360
ttctctccca ggcgccactg gacgacgcaa ggttgcaatt gctctatcta tcccggccat     420
ataacgggtc accgcatggc atgggatatg atgatgaact ggtccctac gacggcgttg     480 gtaatggctc agctgctccg gatcccacaa gccatcttgg acatgatcgc tggtgctcac     540
tggggagtcc tggcgggcat agcgtatttc tccatggtgg ggaactgggc gaaggtcctg     600
gtagtgctgc tgctatttgc cggcgtcgac gcggaaaccc acgtcaccgg gggaagtgcc     660
ggccacactg tgtctggatt tgttagcctc ctcgcaccag gcgccaagca gaacgtccag     720
```

```
ctgatcaaca ccaacggcag ttggcacctc aatagcacgg ccctgaactg caatgatagc    780
ctcaacaccg gctggttggc agggcttttc tatcaccaca agttcaactc ttcaggctgt    840
cctgagaggc tagccagctg ccgacccctt accgattttg accagggctg ggccctatc    900 agttatgcca acggaagcgg ccccgaccag cgcccctact gctggcacta ccccccaaaa    960
ccttgcggta ttgtgcccgc gaagagtgtg tgtggtccgg tatattgctt cactcccagc   1020
cccgtggtgg tgggaacgac cgacaggtcg ggcgcgccca cctacagctg gggtgaaaat   1080 gatacgacg tcttcgtcct taacaatacc aggccaccgc tgggcaattg gttcggttgt   1140
acctggatga actcaactgg attcaccaaa gtgtgcggag cgcctccttg tgtcatcgga   1200
ggggcgggca acaaccccct gcactgcccc actgattgct ccgcaagca tccggacgcc   1260 acatactctc ggtgcggctc cggtccctgg atcacaccca ggtgcctggt cgactacccg   1320
tataggcttt ggcattatcc ttgtaccatc aactacacta tatttaaaat caggatgtac   1380
gtgggagggg tcgagcacag gctggaagct gcctgcaact ggacgcgggg cgaacgttgc   1440
gatctggaag atagggacag gtccgagctc agcccgttac tgctgaccac tacacagtgg   1500
caggtcctcc cgtgttcctt cacaaccctg ccagccttgt ccaccggcct catccacctc   1560
caccagaaca ttgtggacgt gcagtacttg tacggggtgg ggtcaagcat cgcgtcctgg   1620
gccattaagt gggagtacgt cgtcctcctg ttccttctgc ttgcagacgc gcgcgtctgc   1680
tcctgcttgt ggatgatgct actcatatcc aagcggaag cggctttgga gaacctcgta   1740
atacttaatg cagcatccct ggccgggacg cacggtcttg tatccttcct cgtgttcttc   1800
tgctttgcat ggtatctgaa gggtaagtgg gtgcccggag cggtctacac cttctacggg   1860
atgtggcctc tcctcctgct cctgttggcg ttgccccagc gggcgtacgc gtaa         1914

<210> SEQ ID NO 2
<211> LENGTH: 637
<212> TYPE: PRT
<213> ORGANISM: Hepatitis C virus-1

<400> SEQUENCE: 2

Ser Phe Ser Ile Phe Leu Leu Ala Leu Leu Ser Cys Leu Thr Val Pro
  1               5                  10                  15

Ala Ser Ala Tyr Gln Val Arg Asn Ser Thr Gly Leu Tyr His Val Thr
             20                  25                  30

Asn Asp Cys Pro Asn Ser Ser Ile Val Tyr Glu Ala Ala Asp Ala Ile
         35                  40                  45

Leu His Thr Pro Gly Cys Val Pro Cys Val Arg Glu Gly Asn Ala Ser
     50                  55                  60

Arg Cys Trp Val Ala Met Thr Pro Thr Val Ala Thr Arg Asp Gly Lys
 65                  70                  75                  80

Leu Pro Ala Thr Gln Leu Arg Arg His Ile Asp Leu Leu Val Gly Ser
                 85                  90                  95

Ala Thr Leu Cys Ser Ala Leu Tyr Val Gly Asp Leu Cys Gly Ser Val
            100                 105                 110

Phe Leu Val Gly Gln Leu Phe Thr Phe Ser Pro Arg Arg His Trp Thr
        115                 120                 125

Thr Gln Gly Cys Asn Cys Ser Ile Tyr Pro Gly His Ile Thr Gly His
    130                 135                 140

Arg Met Ala Trp Asp Met Met Met Asn Trp Ser Pro Thr Thr Ala Leu
145                 150                 155                 160

Val Met Ala Gln Leu Leu Arg Ile Pro Gln Ala Ile Leu Asp Met Ile
```

-continued

```
                165                 170                 175
Ala Gly Ala His Trp Gly Val Leu Ala Gly Ile Ala Tyr Phe Ser Met
        180                 185                 190
Val Gly Asn Trp Ala Lys Val Leu Val Val Leu Leu Leu Phe Ala Gly
        195                 200                 205
Val Asp Ala Glu Thr His Val Thr Gly Gly Ser Ala Gly His Thr Val
        210                 215                 220
Ser Gly Phe Val Ser Leu Leu Ala Pro Gly Ala Lys Gln Asn Val Gln
225                 230                 235                 240
Leu Ile Asn Thr Asn Gly Ser Trp His Leu Asn Ser Thr Ala Leu Asn
                245                 250                 255
Cys Asn Asp Ser Leu Asn Thr Gly Trp Leu Ala Gly Leu Phe Tyr His
                260                 265                 270
His Lys Phe Asn Ser Ser Gly Cys Pro Glu Arg Leu Ala Ser Cys Arg
                275                 280                 285
Pro Leu Thr Asp Phe Asp Gln Gly Trp Gly Pro Ile Ser Tyr Ala Asn
                290                 295                 300
Gly Ser Gly Pro Asp Gln Arg Pro Tyr Cys Trp His Tyr Pro Pro Lys
305                 310                 315                 320
Pro Cys Gly Ile Val Pro Ala Lys Ser Val Cys Gly Pro Val Tyr Cys
                325                 330                 335
Phe Thr Pro Ser Pro Val Val Gly Thr Thr Asp Arg Ser Gly Ala
                340                 345                 350
Pro Thr Tyr Ser Trp Gly Glu Asn Asp Thr Asp Val Phe Val Leu Asn
                355                 360                 365
Asn Thr Arg Pro Pro Leu Gly Asn Trp Phe Gly Cys Thr Trp Met Asn
                370                 375                 380
Ser Thr Gly Phe Thr Lys Val Cys Gly Ala Pro Pro Cys Val Ile Gly
385                 390                 395                 400
Gly Ala Gly Asn Asn Thr Leu His Cys Pro Thr Asp Cys Phe Arg Lys
                405                 410                 415
His Pro Asp Ala Thr Tyr Ser Arg Cys Gly Ser Gly Pro Trp Ile Thr
                420                 425                 430
Pro Arg Cys Leu Val Asp Tyr Pro Tyr Arg Leu Trp His Tyr Pro Cys
                435                 440                 445
Thr Ile Asn Tyr Thr Ile Phe Lys Ile Arg Met Tyr Val Gly Gly Val
                450                 455                 460
Glu His Arg Leu Glu Ala Ala Cys Asn Trp Thr Arg Gly Glu Arg Cys
465                 470                 475                 480
Asp Leu Glu Asp Arg Asp Arg Ser Glu Leu Ser Pro Leu Leu Leu Thr
                485                 490                 495
Thr Thr Gln Trp Gln Val Leu Pro Cys Ser Phe Thr Thr Leu Pro Ala
                500                 505                 510
Leu Ser Thr Gly Leu Ile His Leu His Gln Asn Ile Val Asp Val Gln
                515                 520                 525
Tyr Leu Tyr Gly Val Gly Ser Ser Ile Ala Ser Trp Ala Ile Lys Trp
                530                 535                 540
Glu Tyr Val Val Leu Leu Phe Leu Leu Leu Ala Asp Ala Arg Val Cys
545                 550                 555                 560
Ser Cys Leu Trp Met Met Leu Leu Ile Ser Gln Ala Glu Ala Ala Leu
                565                 570                 575
Glu Asn Leu Val Ile Leu Asn Ala Ala Ser Leu Ala Gly Thr His Gly
                580                 585                 590
```

```
Leu Val Ser Phe Leu Val Phe Cys Phe Ala Trp Tyr Leu Lys Gly
        595                 600                 605

Lys Trp Val Pro Gly Ala Val Tyr Thr Phe Tyr Gly Met Trp Pro Leu
    610                 615                 620

Leu Leu Leu Leu Leu Ala Leu Pro Gln Arg Ala Tyr Ala
625                 630                 635

<210> SEQ ID NO 3
<211> LENGTH: 21
<212> TYPE: PRT
<213> ORGANISM: Hepatitis C virus-1

<400> SEQUENCE: 3

Gly Ser Ala Ala Arg Thr Thr Ser Gly Phe Val Ser Leu Phe Ala Pro
1               5                   10                  15

Gly Ala Lys Gln Asn
            20

<210> SEQ ID NO 4
<211> LENGTH: 27
<212> TYPE: PRT
<213> ORGANISM: Hepatitis C virus

<400> SEQUENCE: 4

Gln Thr His Thr Thr Gly Gly Gln Ala Gly His Gln Ala His Ser Leu
1               5                   10                  15

Thr Gly Leu Phe Ser Pro Gly Ala Lys Gln Asn
            20                  25

<210> SEQ ID NO 5
<211> LENGTH: 20
<212> TYPE: PRT
<213> ORGANISM: Hepatitis C virus

<400> SEQUENCE: 5

Asp Ala Thr Tyr Ser Arg Cys Gly Ser Gly Pro Trp Ile Thr Pro Arg
1               5                   10                  15

Cys Leu Val Asp
            20

<210> SEQ ID NO 6
<211> LENGTH: 15
<212> TYPE: PRT
<213> ORGANISM: Hepatitis C virus

<400> SEQUENCE: 6

Leu Val Ala Leu Gly Ile Asn Ala Val Ala Tyr Tyr Arg Gly Leu
1               5                   10                  15

<210> SEQ ID NO 7
<211> LENGTH: 15
<212> TYPE: PRT
<213> ORGANISM: Hepatitis C virus

<400> SEQUENCE: 7

Thr Thr Val Arg Leu Arg Ala Tyr Met Asn Thr Pro Gly Leu Pro
1               5                   10                  15

<210> SEQ ID NO 8
<211> LENGTH: 10
<212> TYPE: PRT
<213> ORGANISM: Hepatitis C virus

<400> SEQUENCE: 8
```

-continued

```
Ser Ser Pro Pro Val Val Pro Gln Ser Phe
1               5                   10

<210> SEQ ID NO 9
<211> LENGTH: 16
<212> TYPE: PRT
<213> ORGANISM: Hepatitis C virus

<400> SEQUENCE: 9

Met Ser Tyr Ser Trp Thr Gly Ala Leu Val Thr Pro Cys Ala Ala Glu
1               5                   10                  15

<210> SEQ ID NO 10
<211> LENGTH: 24
<212> TYPE: DNA
<213> ORGANISM: Artificial
<220> FEATURE:
<223> OTHER INFORMATION: CpG 7909 oligodeoxynucleotide

<400> SEQUENCE: 10
tcgtcgtttt gtcgttttgt cgtt                                          24
```